US011576885B2

(12) United States Patent
Cohen

(10) Patent No.: US 11,576,885 B2
(45) Date of Patent: Feb. 14, 2023

(54) COMPOSITIONS AND METHODS FOR THE TREATMENT OF BRAIN INJURY

(71) Applicant: THE CHILDREN'S HOSPITAL OF PHILADELPHIA, Philadelphia, PA (US)

(72) Inventor: Akiva S. Cohen, Bala Cynwyd, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 17/064,000

(22) Filed: Oct. 6, 2020

(65) Prior Publication Data
US 2021/0030704 A1    Feb. 4, 2021

Related U.S. Application Data

(63) Continuation of application No. 14/785,122, filed as application No. PCT/US2014/034142 on Apr. 15, 2014, now abandoned.

(60) Provisional application No. 61/883,526, filed on Sep. 27, 2013, provisional application No. 61/812,352, filed on Apr. 16, 2013.

(51) Int. Cl.
    *A61K 31/198*    (2006.01)
    *A61P 25/00*     (2006.01)
    *A61K 9/00*      (2006.01)

(52) U.S. Cl.
    CPC .......... *A61K 31/198* (2013.01); *A61K 9/0053* (2013.01)

(58) Field of Classification Search
    CPC ...... A61K 31/198; A61K 9/0053; A61P 25/00
    USPC ........................................................ 514/561
    See application file for complete search history.

(56) References Cited

U.S. PATENT DOCUMENTS

| | | |
|---|---|---|
| 5,028,622 A | 7/1991 | Plaitakis |
| 2004/0087490 A1 | 5/2004 | Troup et al. |
| 2005/0064013 A1 | 3/2005 | Liebrech |
| 2008/0260644 A1 | 10/2008 | Cohen |
| 2009/0170786 A1 | 7/2009 | Greenberg |
| 2011/0065715 A1 | 3/2011 | Strittmatter et al. |
| 2018/0133185 A1 | 5/2018 | Cohen |
| 2020/0170986 A1 | 6/2020 | Cohen |

FOREIGN PATENT DOCUMENTS

| | | |
|---|---|---|
| JP | 2000-217547 A | 8/2000 |
| WO | 2007/064618 A1 | 6/2007 |

OTHER PUBLICATIONS

Cole et al. PNAS 2010, 107 (1), 366-371.*
Acuna-Goycolea et al. J. Neurosci. 2004, 24, 3013-3022.*
Karnani et al. Neuron 2011, 72, 616-629.*
Baumann Neurol Med 2012, 14, 205-212.*
Scaini, G., et al., "Chronic administration of branched-chain amino acids impairs spatial memory and increases brain-derived neurotrophic factor in a rat model" J. Inherit. Metab. Dis. (2013) 36:721-730.
Elkind, J.A., et al., "Efficacy, dosage, and duration of action of branched chain amino acid therapy for traumatic brain injury" Front. Neurol. (2015) 6:73.
Russell, K.C., et al., "An fMRI Investigation of Episodic Memory after TBI" J. Clin. Exp. Neuropsychol. (2011) 33(5):538-547.
Haraguchi, T., et al., "Evaluation of the Odour of Aminoleban® EN, Taste-masked with Flavoured Powders, by Human and Electronic Noses," J. Pharm. Pharmacol. (2013) 65(4):503-11.
Mukai, J., et al., "The Effect of Taste-odour Interactions on the Palatability of Nutritional Products for Liver Failure," Asian J. Pharm. Sci. (2009) 4(1):46-55.
Jeter, C.B., et al., "Human Mild Traumatic Brain Injury Decreases Circulating Branched-Chain Amino Acids and Their Metabolite Levels" J. Neurotrauma (2013) 30:671-679.
Blennow, K., et al., "The neuropathology and neurobiology of traumatic brain injury" Neuron (2012) 76(5):886-99.
Erdman, et al., eds. "Nutrition and Traumatic Brain Injury. Improving acute and subacute health outcomes in military personnel" The National Academies Press, Washington DC (2011) pp. 55-68 and 108-114.
Aquilani, R., et al., "Peripheral Plasma Amino Acid Abnormalities in Rehabilitation Patients With Severe Brain Injury" Arch. Phys. Med. Rehabil. (2000) 81:176-181.
Aquilani, R., et al., "Reduced Plasma Levels of Tyrosine, Precursor of Brain Catecholamines, and of Essential Amino Acids in Patients With Severe Traumatic Brain Injury After Rehabilitation" Arch. Phys. Med. Rehabil. (2003) 84:1258-1265.
Aquilani, R., et al., "Branched-Chain Amino Acids Enhance the Cognitive Recovery of Patients With Severe Traumatic Brain Injury" Arch. Phys. Med. Rehabil. (2005) 86:1729-1735.
Aquilani, R., et al., "Branched-Chain Amino Acids May Improve Recovery From a Vegetative or Minimally Conscious State in Patients With Traumatic Brain Injury: A Pilot Study" Arch. Phys. Med. Rehabil. (2008) 89:1642-1647.
Cole, J.T., et al., "Dietary branched chain amino acids ameliorate injury-induced cognitive impairment" PNAS (2010) 107(1):366-371.
Fernstrom, J.D., "Branched-Chain Amino Acids and Brain Function" J. Nutr. (2005) 135:1539S-1546S.
Karnani, M.M., et al., "Activation of Central Orexin/Hypocretin Neurons by Dietary Amino Acids" Neuron (2011) 72:616-629.

(Continued)

*Primary Examiner* — Irina Neagu
(74) *Attorney, Agent, or Firm* — Robert C. Netter, Jr.; Dann, Dorfman, Herrell & Skillman

(57) ABSTRACT

Compositions and methods are provided for the alleviation of pathology induced by traumatic brain injury.

17 Claims, 16 Drawing Sheets

(56) References Cited

OTHER PUBLICATIONS

Figure 1:
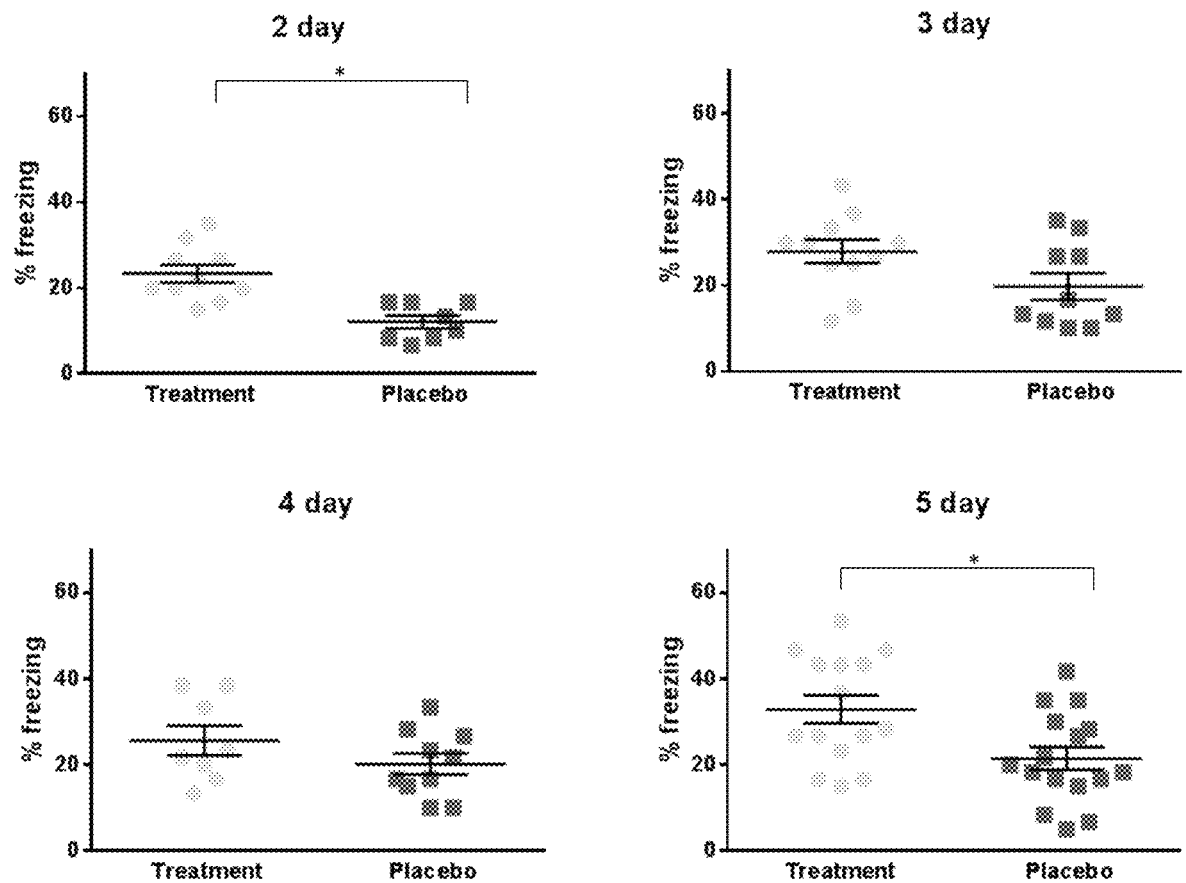

Lim, M.M., et al., "Dietary Therapy Mitigates Persistent Wake Deficits Caused by Mild Traumatic Brain Injury" Sci. Translat. Med. (2013) 5(215):215ra173.
Richardson, M.A., et al., "Efficacy of the Branched-Chain Amino Acids in the Treatment of Tardive Dyskinesia in Men" Am. J. Psychiatry (2003) 160:1117-1124.
Scarna, A., et al., "Effects of a branched-chain amino acid drink in mania" Brit. J. Psych. (2003) 182:210-213.
Witgen, B.M., et al., "Regional Hippocampal Alteration Associated With Cognitive Deficit Following Experimental Brain Injury: A Systems, Network and Cellular Evaluation" Neuroscience (2005) 133:1-15.
Arun, P., et al., "Metabolic Acetate Therapy for the Treatment of Traumatic Brain Injury" J. Neurotrauma (2010) 27:293-298.
Johnson, V.E., et al., "Widespread τ and amyloid-β pathology many years after a single traumatic brain injury in humans" Brain Pathol. (2012) 22(2):142-9.
Mennella, et al., "Modification of bitter taste in children" Dev. Psychobiol. (2003) 43(2):120-7.
Itou, et al., "Heating improves poor compliance with branched chain amino acid-rich supplementation in patients with liver cirrhosis: A before-after pilot study" Mol. Med. Rep. (2009) 2:983-987.
Lindqvist, M., "Flavour Improvement of Water Solutions Comprising Bitter Amino Acids" Swedish University of Agricultural Sciences, Uppsala, Sweden (2010).
Jungbunzlauer, "Product Range: Bio-based ingredients" Basel, Switzerland (2017), available at www.jungbunzlauer.com/fileadmin/content/_PDF/PRINT_PROJECTS/Product_Range/JBL_FO_Product_Range_2017-217.pdf.
Gusman, H.J., et al., "A dose-finding study on the effects of branch chain amino acids on surrogate markers of brain dopamine function" Psychopharmacology (2002) 160:192-197.
Singer, R., "New Ways for Beverage Formulators to Reduce Bitterness and Balance Sourness" Jungbunzlauer (2011).
Palmer, et al., "Efficacy and Longevity of Dietary Therapy for Brain Injury" Neuoscience (2012) Presentation Abstract, New Orleans, LA.

\* cited by examiner

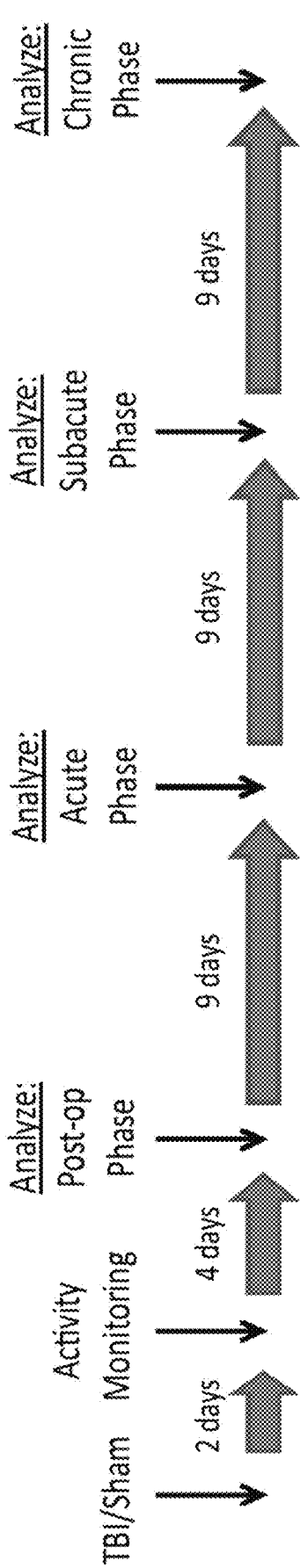
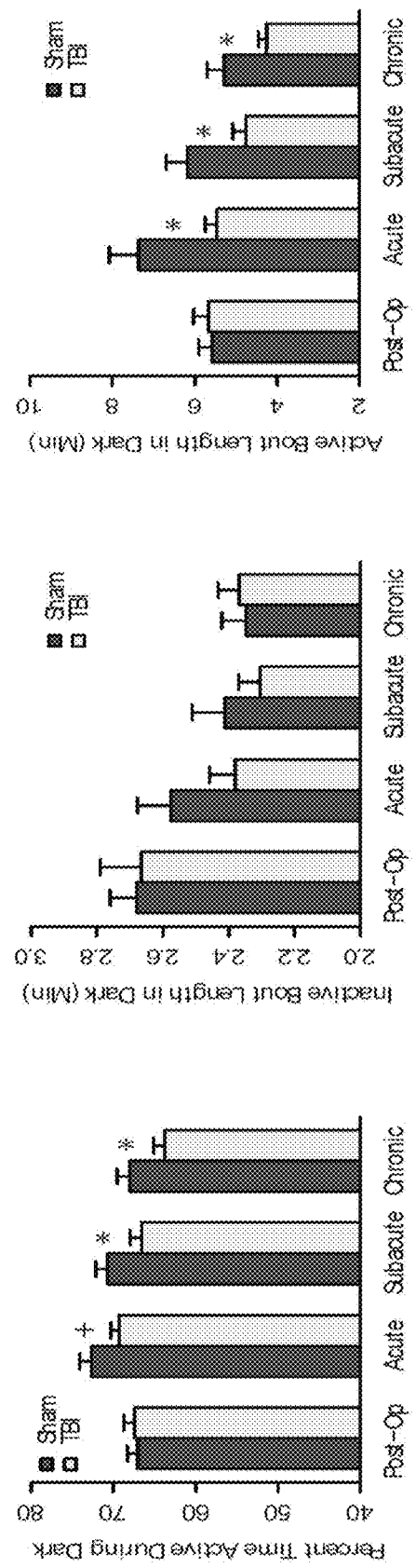
FIG. 6A
FIG. 6B
FIG. 6C
FIG. 6D

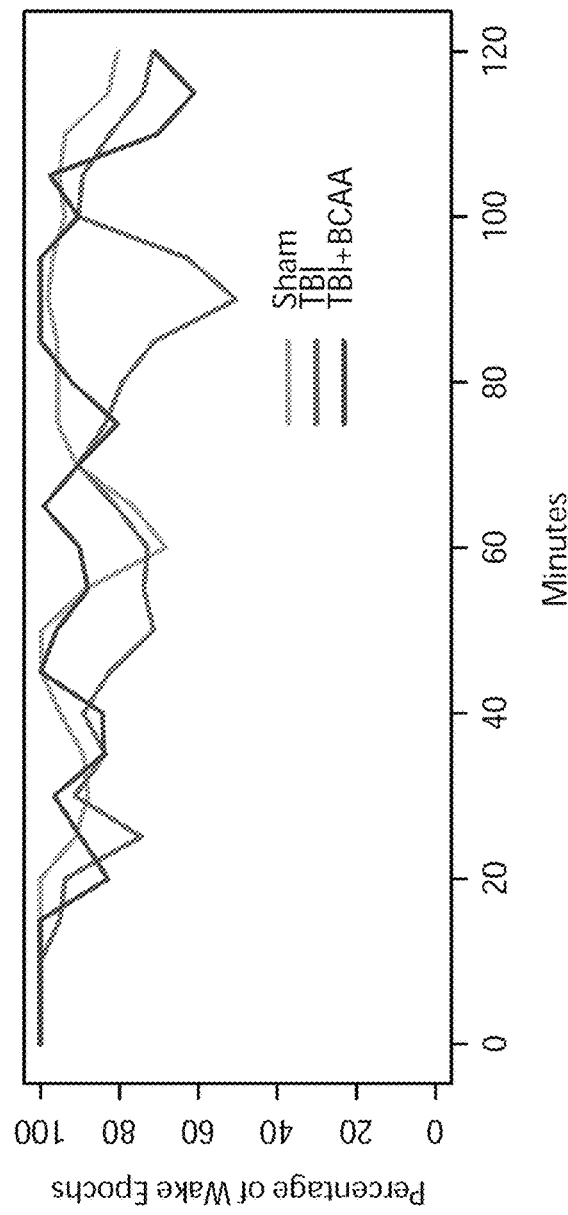
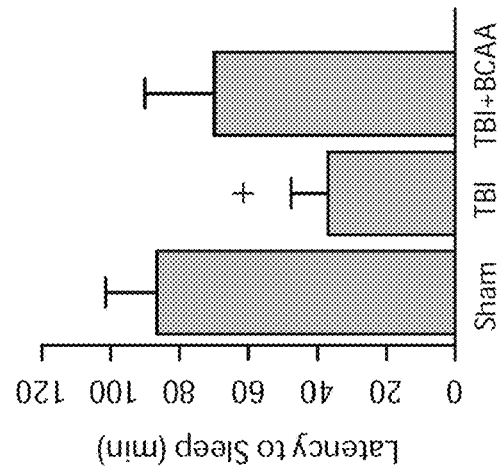
FIG. 11B
FIG. 11A

COMPOSITIONS AND METHODS FOR THE TREATMENT OF BRAIN INJURY

This application is a continuation application of U.S. patent application Ser. No. 14/785,122, filed Oct. 16, 2015, which is a § 371 application of PCT/US2014/034142, filed Apr. 15, 2014, which claims priority under 35 U.S.C. § 119(e) to U.S. Provisional Application No. 61/883,526, filed on Sep. 27, 2013, and U.S. Provisional Application No. 61/812,352, filed on Apr. 16, 2013. The foregoing applications are incorporated by reference herein.

This invention was made with government support under grant nos. NS069629 and HD059288 awarded by the National Institutes of Health. The government has certain rights in the invention.

FIELD OF THE INVENTION

The present invention relates to the alleviation of pathology associated with brain damage, particularly traumatic brain injury.

BACKGROUND OF THE INVENTION

Traumatic brain injury (TBI) afflicts up to two million people annually in the United States, and is the primary cause of death and disability in young adults and children. TBI results in long-lasting cognitive impairment and currently there are no effective therapies to mitigate or rectify this pathology. TBI often causes enduring disabilities including emotional alterations, cognitive impairment and memory dysfunction. These functional deficits result from changes in hippocampal network excitability that are precipitated by regional imbalances between excitatory and inhibitory synaptic activity, including decreased network excitability in area CA1 and increased excitability in the dentate gyms. Furthermore, both neuronal and astrocytic metabolism following injury are altered, including increased accumulation of lactate and an increase in intracellular glutamate, but the interaction between astrocyte-derived metabolites and neuronal metabolism following injury is not fully understood. New methods of treatment for the inhibition and/or prevention of the pathology associated with traumatic brain injury are needed.

SUMMARY OF THE INVENTION

In accordance with the instant invention, methods for inhibiting, reducing, treating, and/or preventing in a subject the pathology associated with traumatic brain injury are provided. In a particular embodiment, the method comprises administering to the subject at least one branched chain amino acid (BCAA), particularly all three branched chain amino acids. In a particular embodiment, BCAAs are administered orally.

In accordance with another aspect of the instant invention, compositions comprising the branched chain amino acids and, optionally, at least one pharmaceutically acceptable carrier are provided. The compositions may be in an orally acceptable form such as a liquid or powder (e.g., lyophilized) form.

In accordance with another aspect of the instant invention, methods for treating a sleep disorder associated with traumatic brain injury in a subject are provided. The methods comprise administering to the subject at least one branched chain amino acid, particularly valine, leucine, and isoleucine. The branched chain amino acids may be administered in a composition with a pharmaceutically acceptable carrier, such as the oral compositions of the instant invention.

BRIEF DESCRIPTIONS OF THE DRAWING

FIG. 1 provides a graph of freezing percentage in a conditioned fear response (CFR) assay of mice receiving BCAA diet (treatment) or receiving placebo without the BCAA diet (placebo) for 2, 3, 4, or 5 days after fluid percussion injury.

Figure 2:
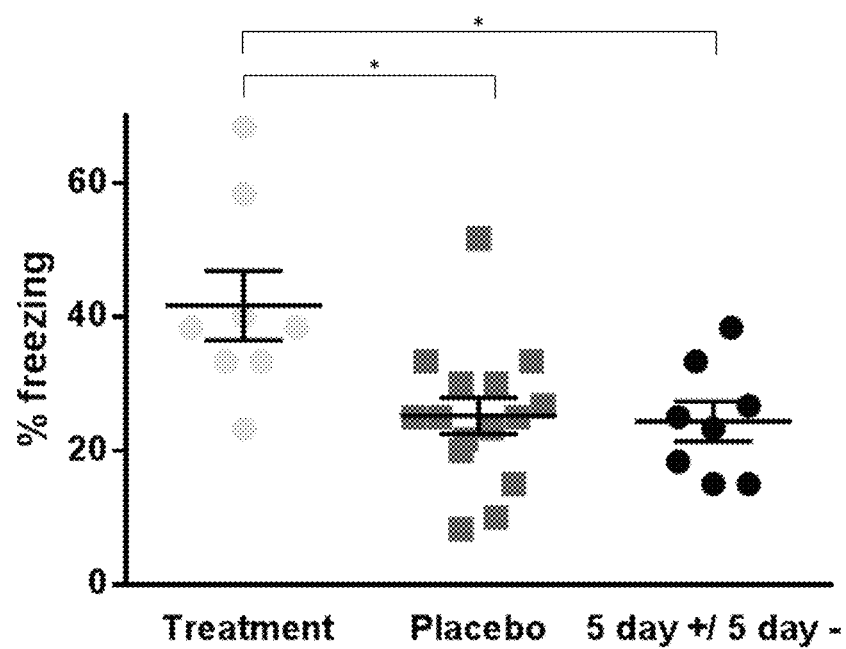

FIG. 2 provides a graph of freezing percentage in a CFR assay of mice receiving BCAA diet for 10 days (treatment), brain injured animals without the BCAA diet for 10 days (placebo), or on the BCAA diet for 5 days and then without for 5 days (5 day+/5 day−) after fluid percussion injury.

Figure 3:
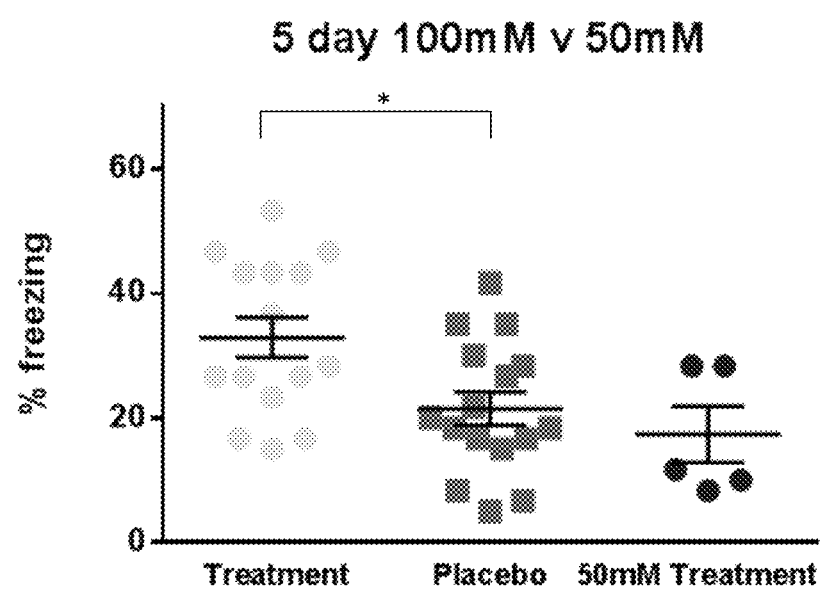

FIG. 3 provides a graph of freezing percentage in a CFR assay of mice receiving BCAA diet at 100 mM or 50 mM (treatment) or controls without the BCAA diet (placebo) for 5 days after fluid percussion injury.

Figure 4:
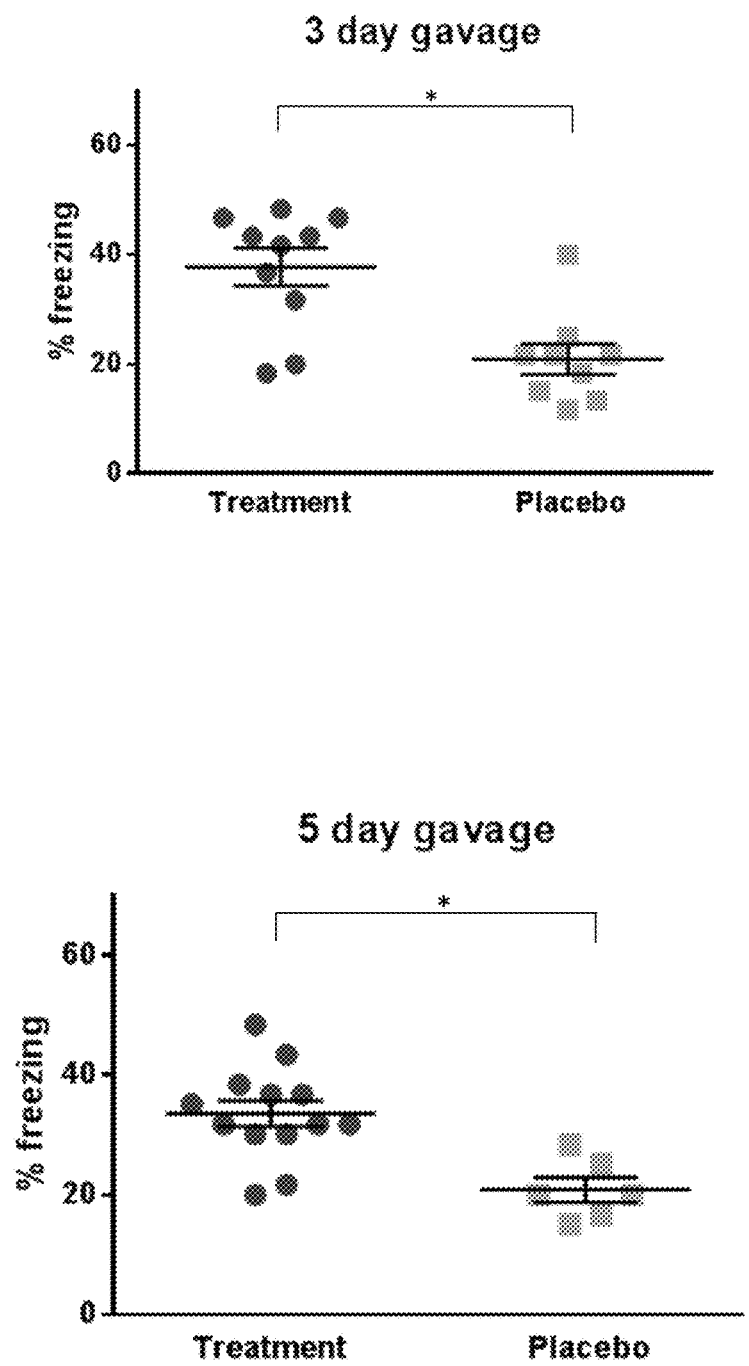

FIG. 4 provides a graph of freezing percentage in a CFR assay of mice receiving BCAA diet via gavage (treatment) or controls without the BCAA diet (placebo) for 3 or 5 days after fluid percussion injury.

Figure 5:
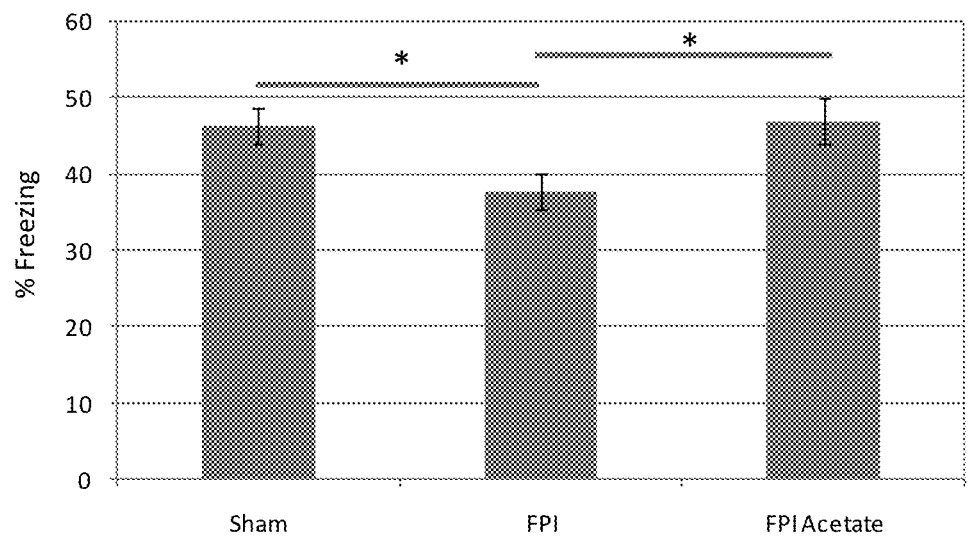

FIG. 5 provides a graph of freezing percentage in a CFR assay of sham mice, mice receiving glyceryl triacetate (GTA) via gavage after injury (FPI acetate) or controls without the GTA diet after injury (FPI) for 5 days after fluid percussion injury. $*P<0.05$.

Figures 6E, 6F:
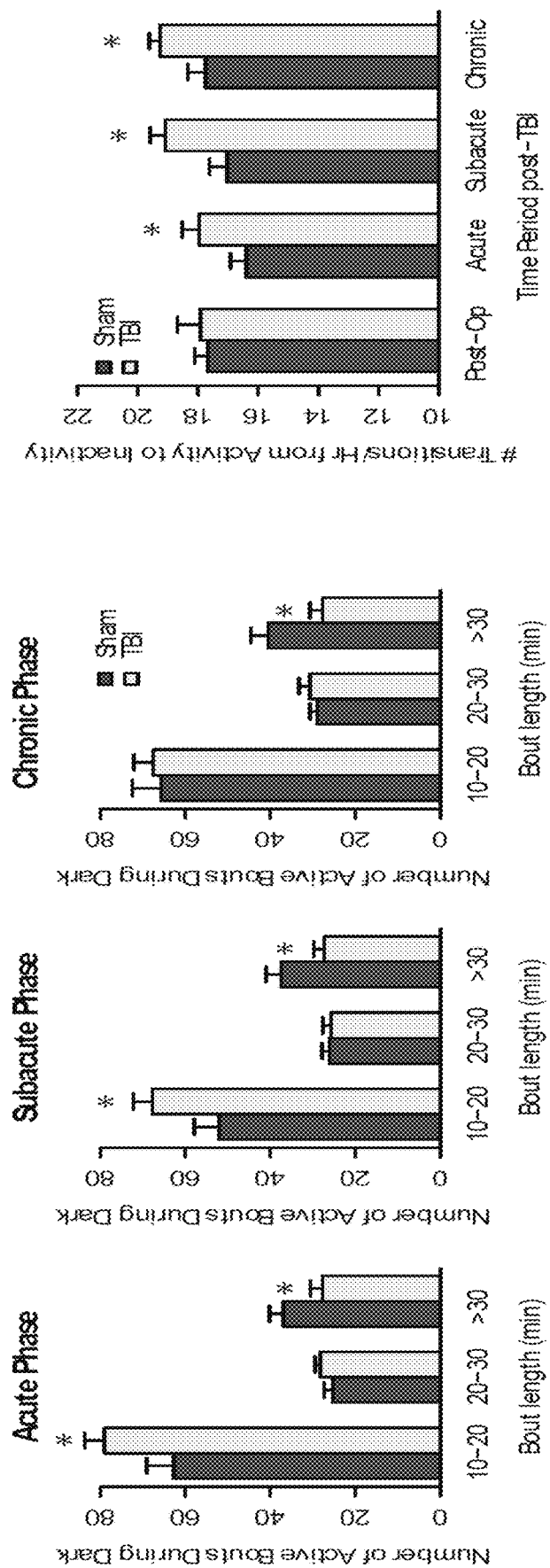

FIG. 6A provides the activity monitoring timeline. Activity patterns were binned into post-op, acute, subacute and chronic time points following injury or sham surgery. FIG. 6B shows the percent time spent active during the dark phase is decreased across acute, subacute and chronic periods after TBI. The average length of each inactivity bout did not significantly differ between groups (FIG. 6C). However, the average length of each activity bout was significantly decreased after TBI across the three time points (FIG. 6D). Active bouts longer than 30 minutes were particularly affected after TBI across all three phases (FIG. 6E). The number of transitions from active to inactive bouts was significantly increased after TBI across the three time points (FIG. 6F). $+p<0.1$, $*p<0.05$.

Figure 7:
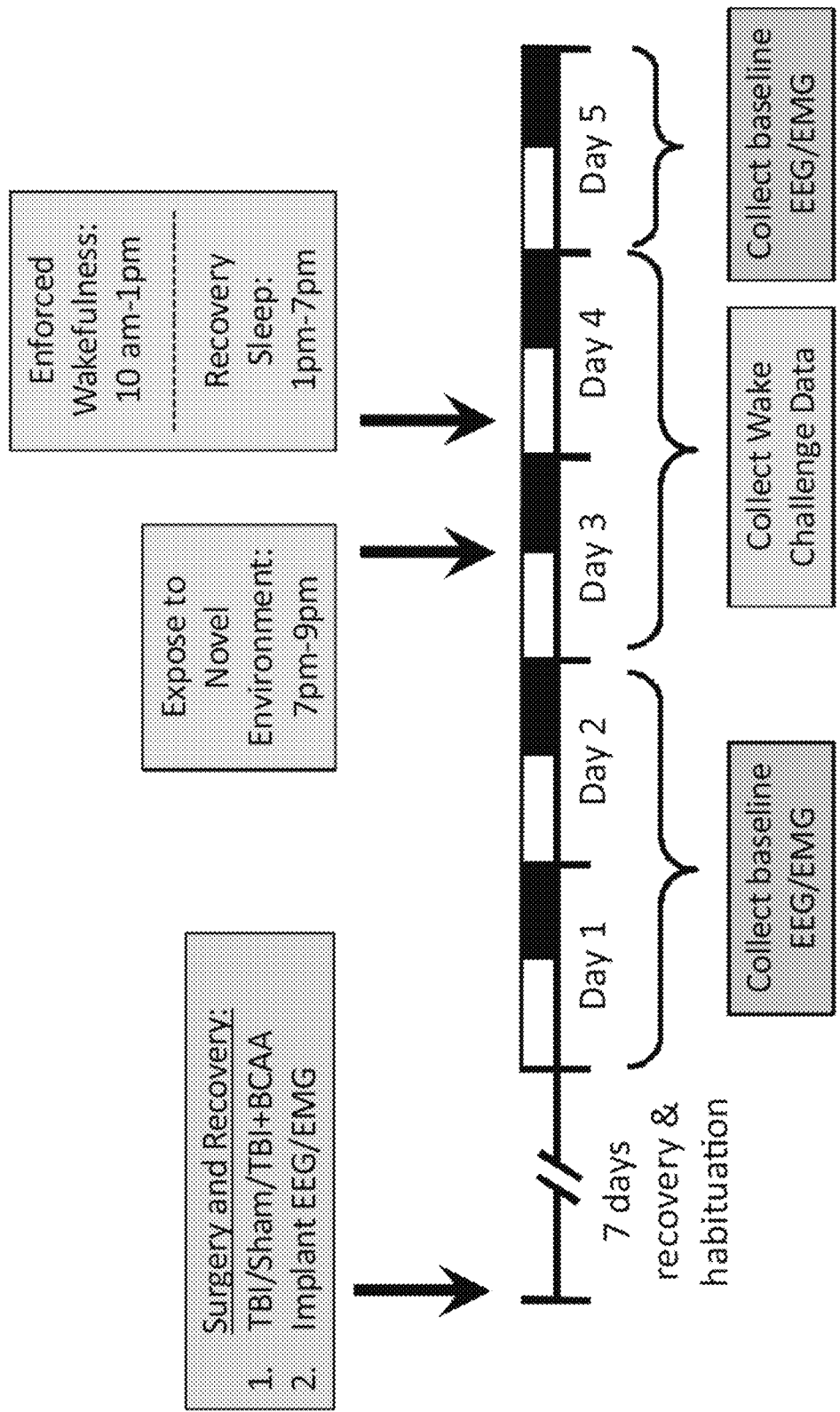

FIG. 7 provides the experimental timeline for EEG/EMG recording.

Figure 8A:
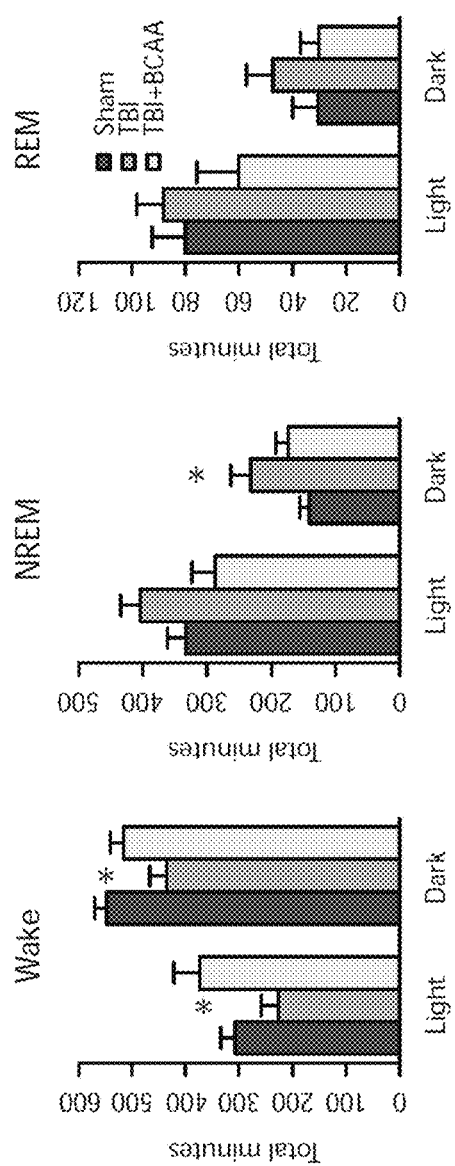
Figure 8B:
Figure 8C:
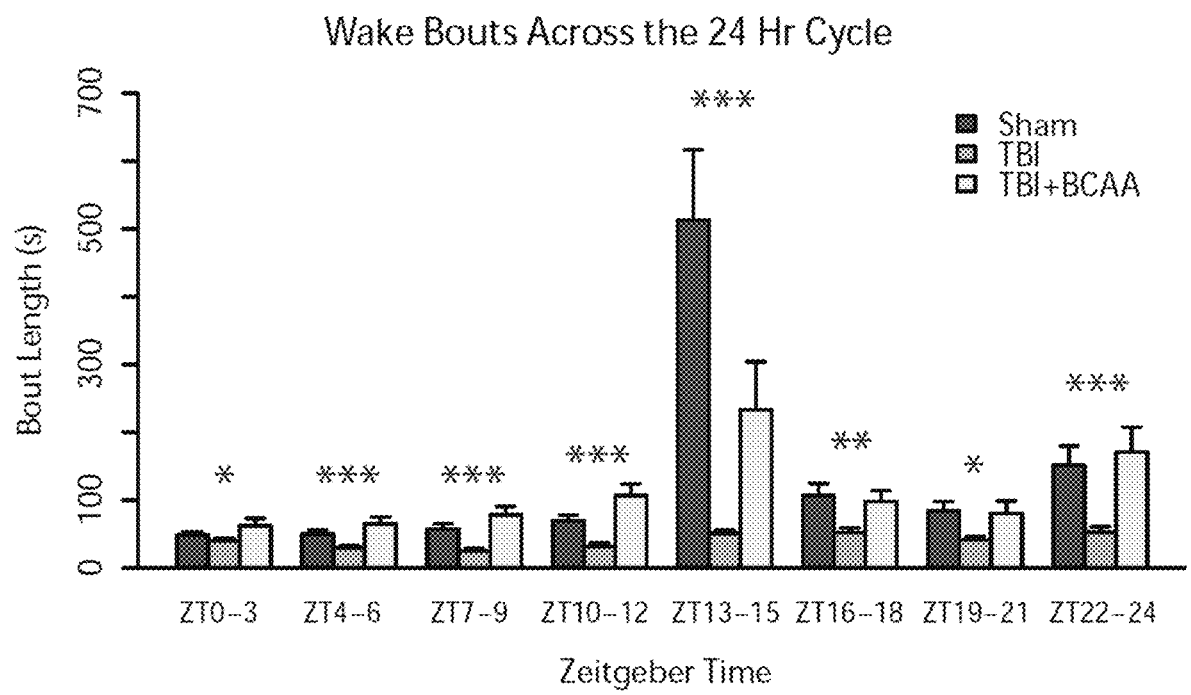
Figure 8D:
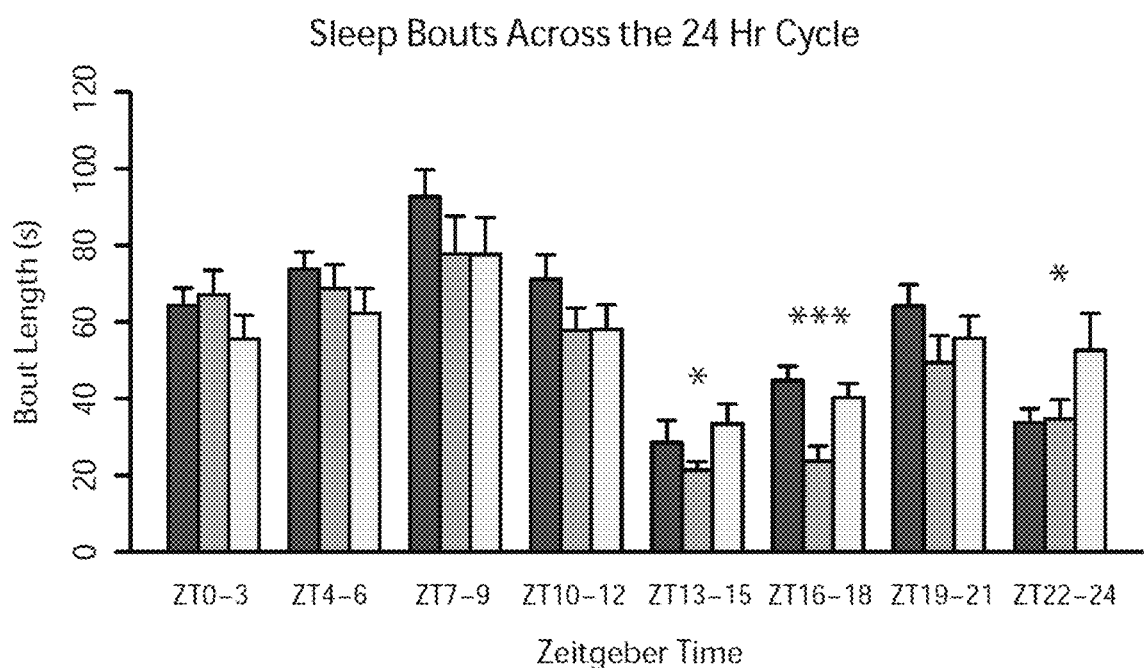

FIGS. 8A-8D show that baseline EEG recordings over 24 hours show significant alterations in wake and sleep patterns, which are ameliorated by BCAA dietary intervention. TBI mice spend less time awake and more time in NREM sleep (FIG. 8A). FIG. 8B provides representative hypnograms from Sham, TBI and TBI+BCAA mice. Note the absence of the long wake period at 19:00 (Lights Off) in the TBI mouse that is restored in TBI+BCAA mouse. FIG. 8C provides the distribution of wake bout length over the circadian cycle shows that TBI significantly shortens wake bouts throughout the light and dark phases, and the normal diurnal fluctuation in wake bout length is abolished. FIG. 8D provides the distribution of sleep (NREM+REM) bout length over the circadian cycle shows significantly shorter sleep bouts in TBI mice during the dark phase. ZT=Zeitgeber Time; ZT0-3=7:00 AM-10:00 AM, ZT13-15=7:00 PM-10:00 PM, and so forth. $*p<0.05$, $p<0.01$, $*p<0.001$.

Figure 9A:
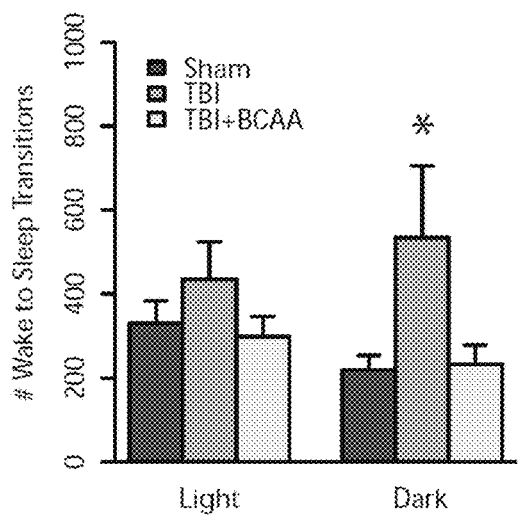
Figure 9B:
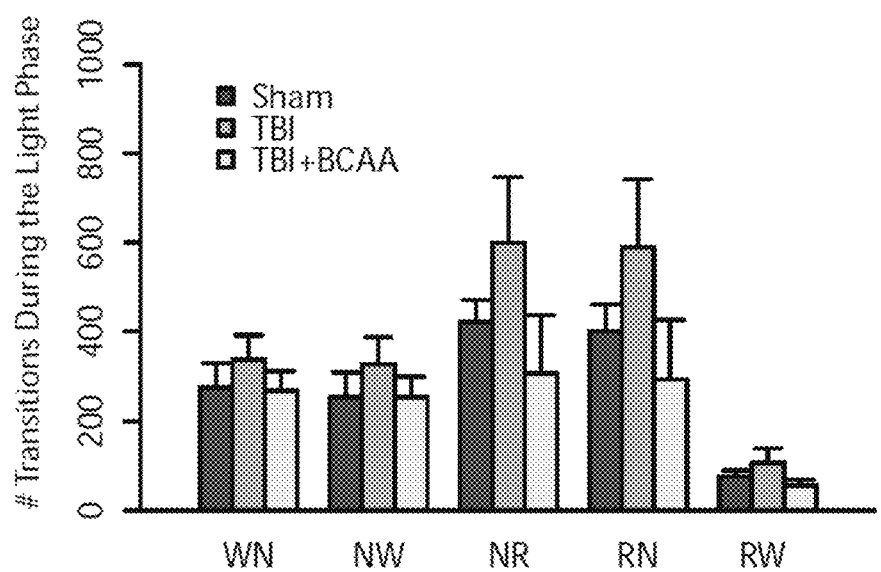
Figure 9C:
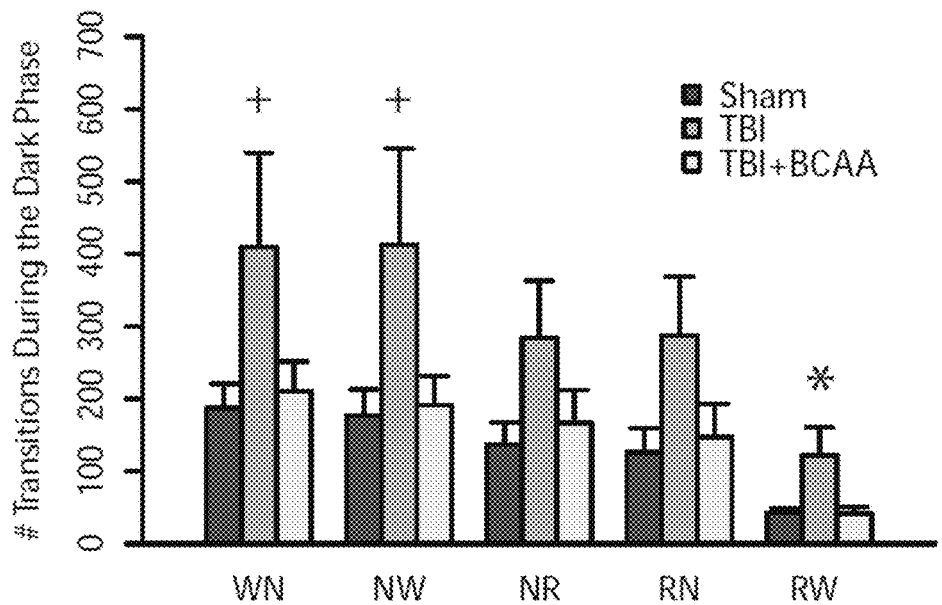
Figure 9D:
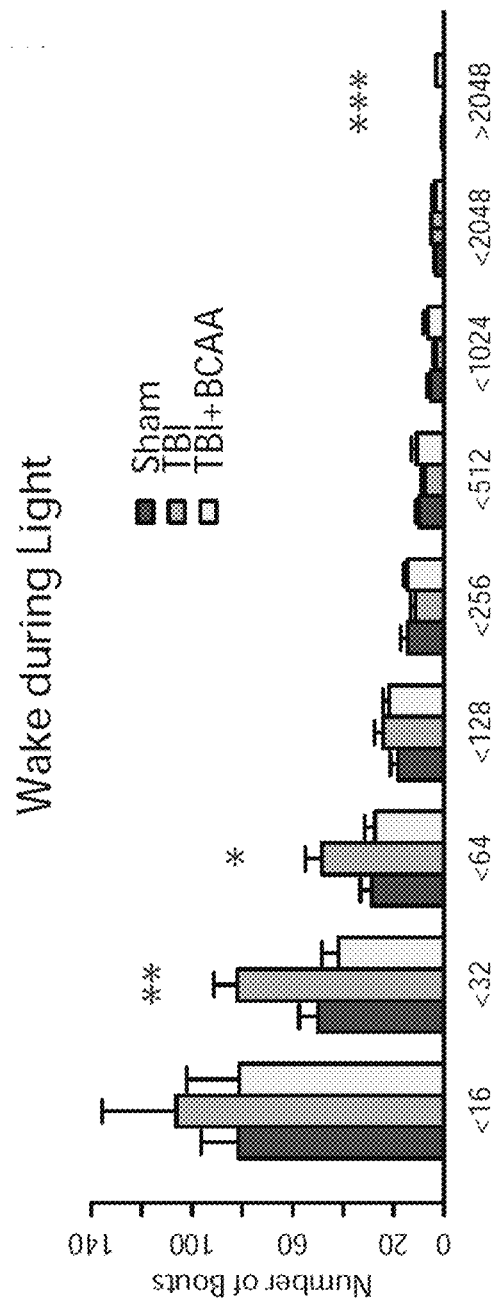
Figure 9E:
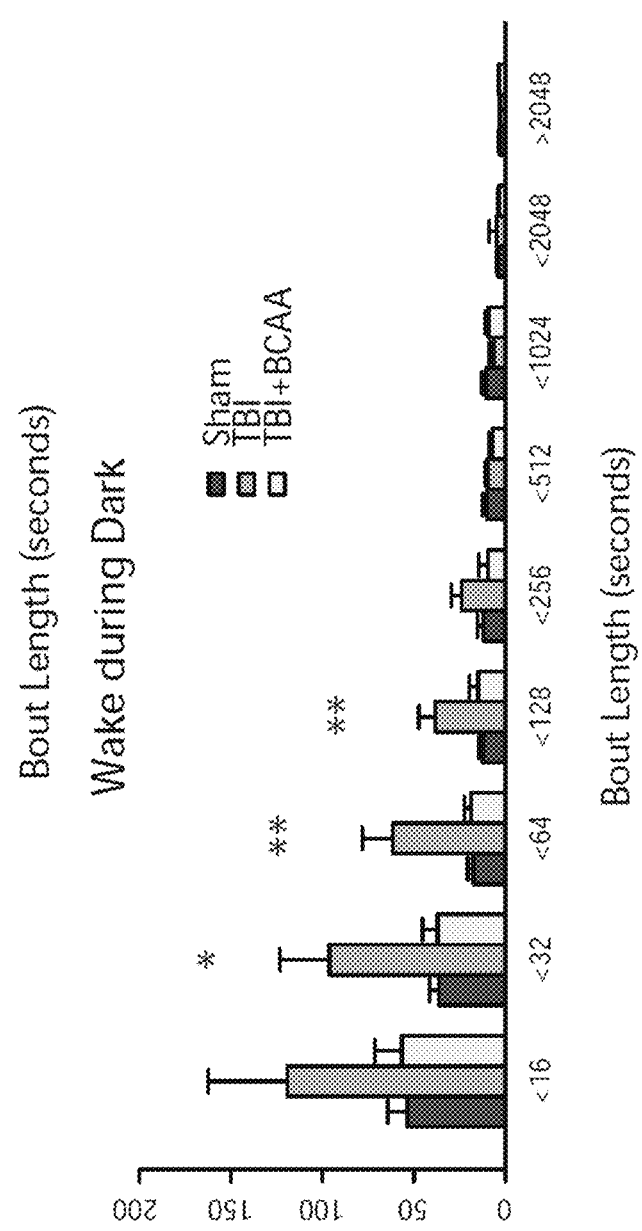

FIGS. 9A-9E show that TBI causes significant behavioral state instability, which is restored by BCAA therapy. TBI significantly increases the total number of wake to sleep (NREM+REM) transitions during the dark, or active phase (FIG. 9A). FIG. 9B shows the transitions sub-categorized by Wake to NREM (WN), NREM to Wake (NW), NREM to REM (NR), REM to NREM (RN), and REM to Wake (RW) during the light phase. FIG. 9C shows the transitions subcategories during the dark phase. Note TBI mice have more transitions to and from Wake (WN, NW, RW), and this is restored by BCAA therapy. Also, group differences are more robust in the dark phase compared to the light phase. TBI mice have significantly more short wake bouts compared to Sham mice, and BCAA therapy restores the distribution of long wake bouts. FIGS. 9D and 9E show that group differences in wake bout lengths are more robust in the dark phase compared to the light phase. $+p<0.1$, $*p<0.05$.

Figure 10A:
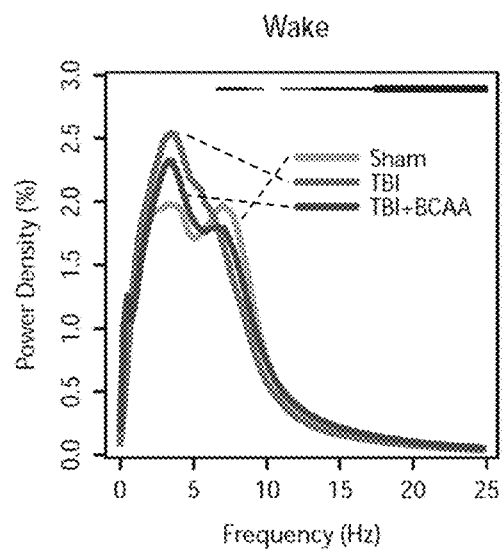
Figure 10A:
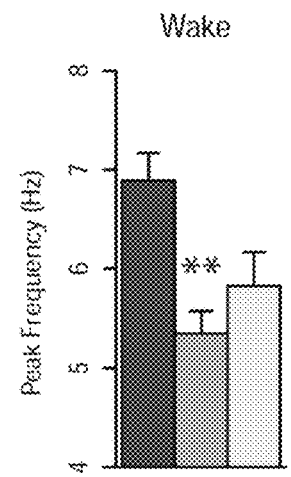
Figure 10B:
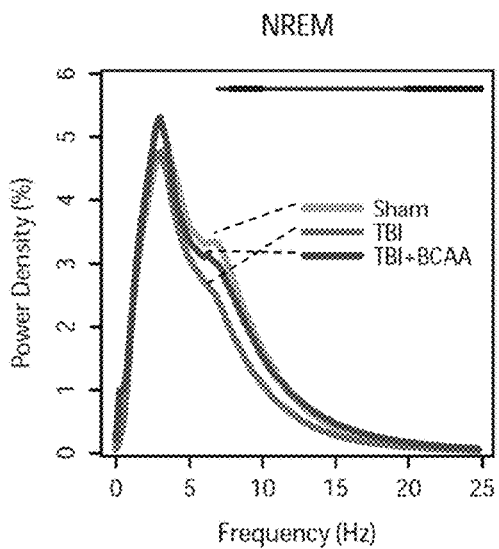
Figure 10B:
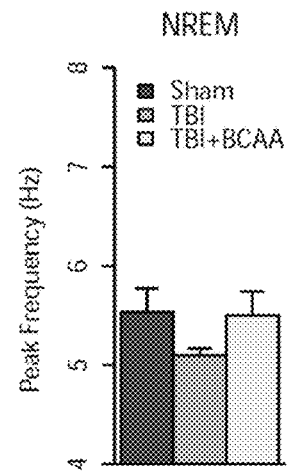
Figure 10C:
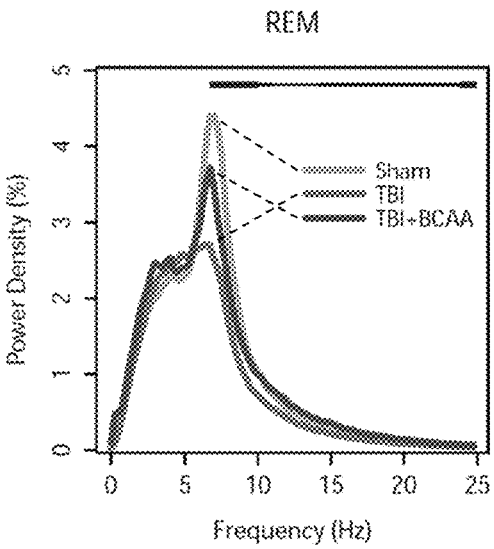
Figure 10C:
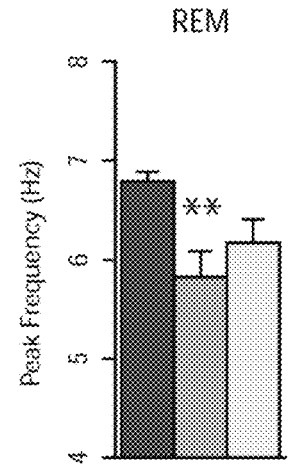

FIG. 10A provides wake power spectra. Statistical group differences denoted as a black bar above the power spectral curves from 7 to 24 Hz. Note the significant left shift in theta peak frequency (TPF) after TBI. FIG. 10B provides NREM power spectra. Group differences are denoted as a black bar above the power spectral curves from 7 to 24 Hz. FIG. 10C provides REM power spectra. Group differences are denoted as a black bar above the power spectral curves again ranging from 7-24 Hz. Again, there is a significant left shift in TPF after TBI. Thin black bar, $p<0.10$, medium black bar, $p<0.05$, thick black bar, $p<0.01$; $**p<0.01$.

FIG. 11A shows that after being placed in novel environment, TBI mice have a shorter latency to the first sleep episode which is reinstated with BCAA therapy. FIG. 11B shows the percentage of epochs scored as wake across 5 minute bins was calculated, and shows that TBI mice have less wake epochs throughout the 2 hour challenge. BCAA therapy restores wakefulness during the novel environment challenge. $+p<0.10$.

Figure 12B:
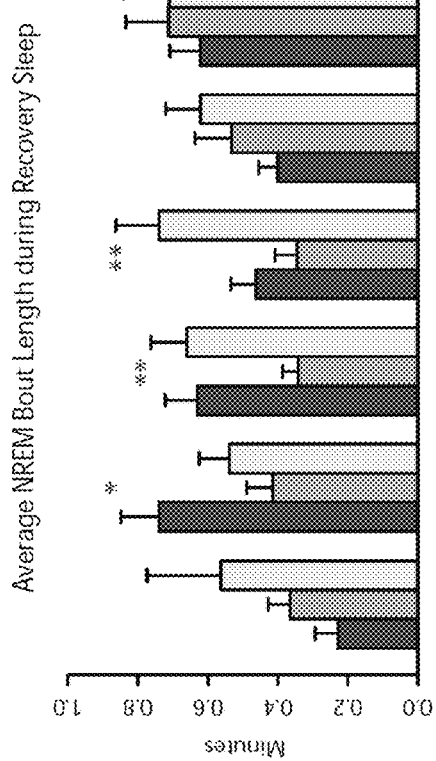
Figure 12D:
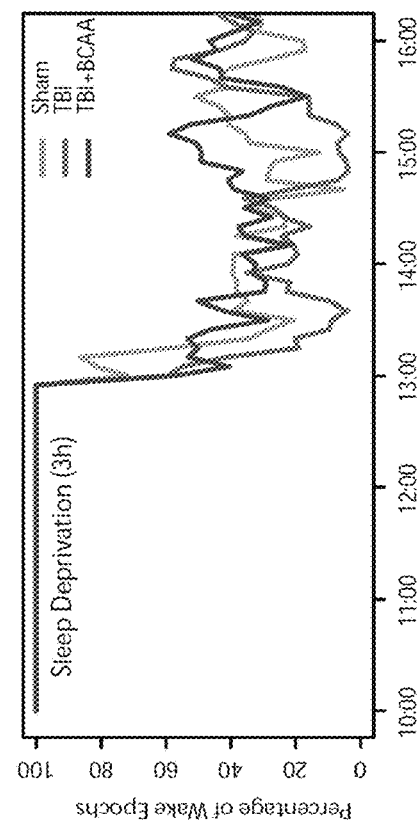
Figure 12A:
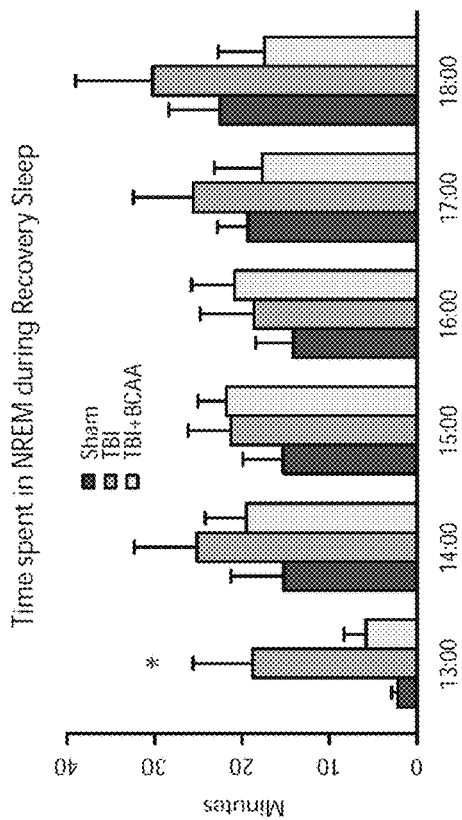
Figure 12C:
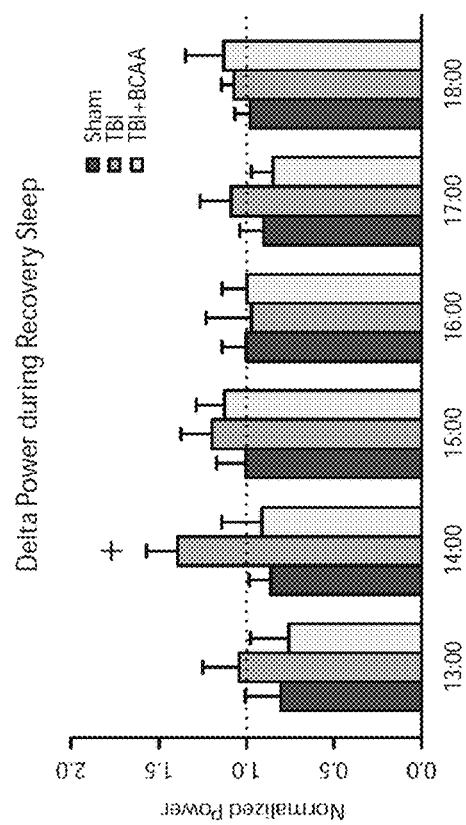

FIGS. 12A-12D show TBI mice show a higher sleep pressure after sleep deprivation. After a relatively short 3 hour period of sleep deprivation, TBI mice spend more time in NREM sleep during the recovery period. BCAA therapy decreases NREM sleep to Sham levels (FIG. 12A). BCAA therapy also restored NREM bout length to sham levels (FIG. 12B). FIG. 12C shows the delta power, indicating a higher sleep pressure, during recovery sleep. FIG. 12D shows that TBI mice also have a lower percentage of wakefulness during the recovery period after sleep deprivation. $+p<0.10$, $*p<0.05$, $**p<0.01$.

Figure 13A:
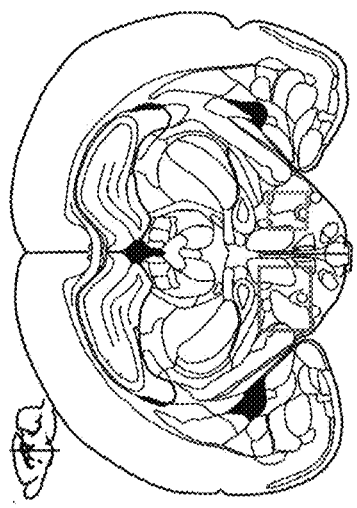
Figure 13B:
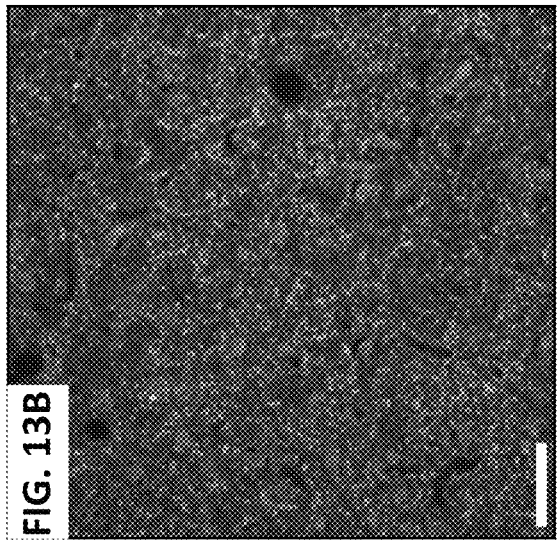
Figure 13C:
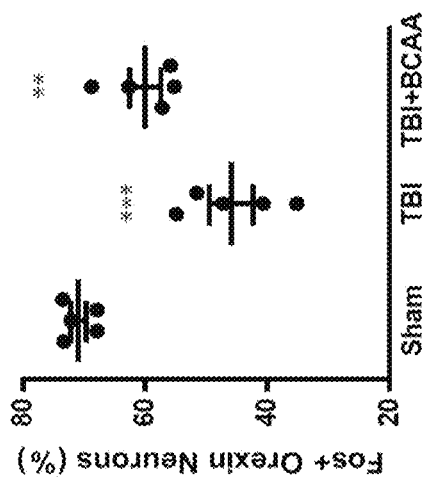
Figure 13D:
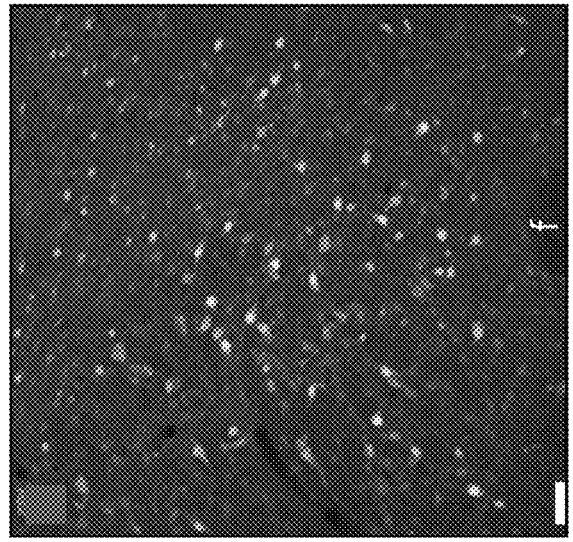
Figure 13E:
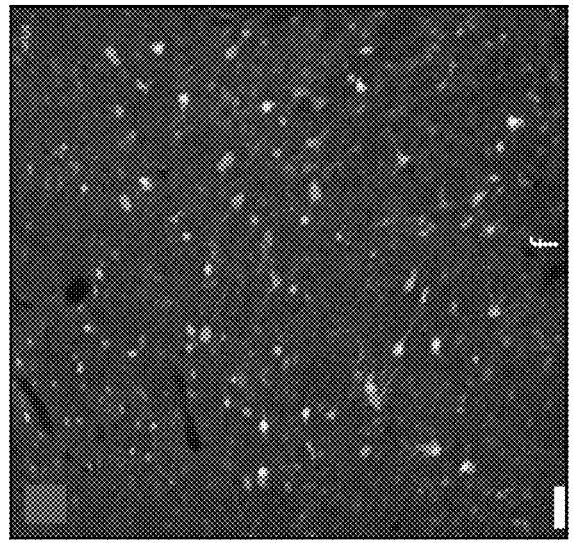
Figure 13F:
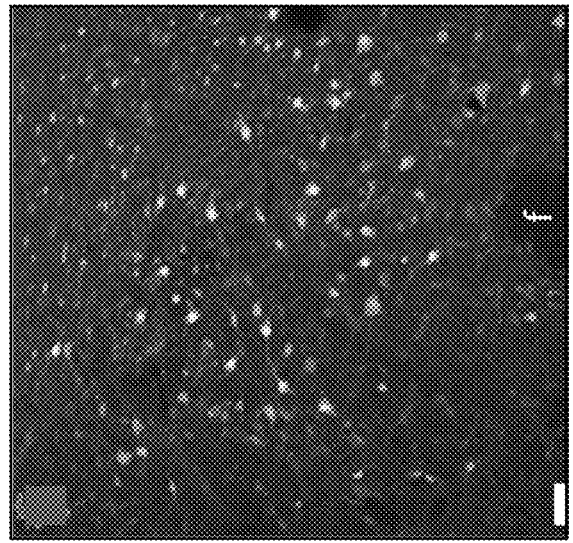

FIG. 13A provides a schematic coronal section from mouse brain showing the lateral hypothalamus (LH, left box), the region where orexin neurons reside and where orexin cells were counted. The right box represents the area depicted in photomicrographs in FIGS. 13D, 13E, and 13F. FIG. 13B provides a photomicrograph of LH showing presynaptic glutamate vesicles (VGLUT1 immunolabeling) in close proximity to orexin cell bodies (orexin-A immunolabeling) at 40x. FIG. 13C provides the quantification of Fos-positive orexin neurons, which are a marker of neural activation after the 3 hour wake challenge, showing significantly decreased orexin activation after TBI compared to Sham mice, which is restored with BCAA therapy (F=22.47, $p<0.0001$; TBI v. Sham $p<0.001$, TBI v. TBI+BCAA $p<0.01$; one-way ANOVA followed by Dunnett's post-hoc tests). FIGS. 13D, 13E, and 13F provide representative photos of LH from Sham, TBI, and TBI+BCAA mice showing orexin colocalization with Fos at 20x. f=fornix. Scale bar=50 um. $p<0.01$, $*p<0.001$.

DETAILED DESCRIPTION OF THE INVENTION

Studies in mice have demonstrated that the hippocampus, a brain structure involved in learning and memory and often injured in concussion, has reduced levels of the three branched chain amino acids (BCAAs) valine, isoleucine and leucine after traumatic brain injury. Dietary administration of BCAAs restored the concentrations of these amino acids in the injured hippocampus, and restored cognitive function to levels not significantly different to non-injured animals.

Dietary BCAA administration has been studied extensively in healthy people and in a variety of disease states over many decades (Fernstrom, J. D. (2005) J. Nutr., 135: 1539S-1546S). BCAA therapy has been studied as it relates to exercise physiology, hepatic pathology, and various neurological and psychiatric disorders (Richardson et al. (2003) Am. J. Psychiatry 160:1117-1124; Richardson et al. (1999) Psychopharmacol., 143:358-364; Tandan et al. (1996) Neurology 47:1220-1226; Mori et al. (2002) J. Neurol. Sci., 195:149-152; Mori et al. (1999) Intern. Med., 38:401-406; Scarna et al. (2003) Br. J. Psychiatry 182:210-213). Patients have been treated with BCAA's for variable lengths of time including chronically for more than 2 years (Muto et al. (2005) Clin. Gastroenterol. Hepatol., 3:705-713). BCAA's have been given orally and as an intravenous infusion (Aquilani et al. (2005) Arch. Phys. Med. Rehabil., 86:1729-1735; Aquilani et al. (2008) Arch. Phys. Med. Rehab., 89:1642-1647; Kirvela et al. (1998) Pharmacol. Biochem. Behav., 60:77-82). The dosing used in these previous studies ranges from a few grams per day to over 100 g/d (Tangkijvanich et al. (2000) Southeast Asian J. Trop. Med. Public Health 31:152-157; Kuroda et al. (2010) J. Gastroenterol. Hepatol., 25:1550-1555). For example, oral doses of 60 g/d have been shown to be effective in reducing mania symptoms (Scarna et al. (2003) Br. J. Psychiatry 182:210-213). Benefit has also been seen in tardive dyskinesia (~15 g/d), spinocerebellar degeneration (6 g/d), anorexia in cancer patients (14 g/d), and hepatic encephalopathy (median amount of BCAA over 11 randomized trials was 28 g/d, with the range of 11 to 57 g/d) (Richardson et al. (2003) Am. J. Psychiatry 160:1117-1124; Richardson et al. (1999) Psychopharmacol., 143:358-364; Mori et al. (2002) J. Neurol. Sci., 195:149-152; Mori et al. (1999) Intern Med., 38:401-406; Cangiano et al. (1996) J. Natl. Cancer Inst., 88:550-552; Als-Nielsen et al. (2003) Cochrane Database Syst. Rev., 2003:CD001939).

Several review papers have examined these studies and summarized the infrequent adverse events (Als-Nielsen et al. (2003) Cochrane Database Syst. Rev., 2003:CD001939; Fernstrom, J. D. (2005) J. Nutr., 135:1539S-1546S). Overall, BCAA's are well tolerated and are associated with minimal to no side effects. There are reports of mild gastrointestinal side effects such as abdominal distention, diarrhea, and constipation. No serious or life threatening side effects have been reported. These studies indicate that humans can consume BCAA's in considerable amounts without adverse effects and, in some cases, with significant benefit to the study populations. Indeed, athletes already consume BCAA's as over the counter nutritional supplements to augment their exercise program.

There are several clinical studies of BCAA use in children. Studies to determine the mean BCAA requirement in healthy school age children and children with mild-to-moderate chronic cholestatic liver disease were conducted by giving children varying amounts of BCAA's (Mager et al. (2003) J. Nutr., 133:3540-3545; Mager et al. (2006) J. Nutr., 136:133-139). BCAA's have been administered safely to children with phenylketonuria in an attempt to inhibit entry of phenylalanine into the brain and reduce its toxic effects on the central nervous system (Berry et al. (1982) Ped. Res., 16:751-755; Berry et al. (1990) Am. J. Dis. Child, 144:539-543; Jordan et al. (1985) Dev. Med. Child Neurol., 27:33-39). Beneficial effects were also seen when children with end-stage liver disease awaiting transplantation were fed with a BCAA-enriched formula compared with a standard formula (Chin et al. (1992) Amer. J. Clin. Nutr., 56:158-163; Chin et al. (1990) J. Gastroenterol. Hepatol., 5:566-572). Symptoms of tardive dyskinesia were reduced in children and adolescents after treatment with BCAA's, and epileptic children treated with up to 20 g/d of BCAA's in conjunction with a ketogenic diet showed reduction in seizure frequency and improvement in behavior and cognitive functioning (Richardson et al. (2004) J. Clin. Psychiatry 65:92-96; Evangeliou et al. (2009) J. Child Neurology 24:1268-1272). In all studies of children and adolescents treated with BCAA's, the supplements were well tolerated and without side effects.

A limited number of studies have examined the efficacy of BCAA's in humans after TBI. One study evaluated plasma amino acid concentrations in patients admitted to a rehabilitation facility approximately two months after TBI and found significantly reduced levels of BCAA's, among other amino acids, relative to age-matched, non-injured controls (Aquilani et al. (2000) Arch. Phys. Med. Rehab., 81:176-181). A follow-up study on a subsequent cohort of TBI patients found that plasma concentrations of amino acids were still reduced 120 days after injury, mainly driven by lower valine levels (Aquilani et al. (2003) Arch. Phys. Med. Rehab., 84:1258-1265). Work by the same group demonstrated that intravenous BCAA's administered to patients in the rehabilitation stage after severe TBI improved disability rating scale scores when compared to placebo (Aquilani et al. (2005) Arch. Phys. Med. Rehab., 86:1729-1735). Additionally, they showed that BCAA's might improve recovery from a post-traumatic vegetative or minimally conscious state (Aquilani et al. (2008) Arch. Phys. Med. Rehab., 89:1642-1647).

The instant invention provides a BCAA rich composition, particularly a liquid consumable, for treatment of cognitive impairment associated with concussion. In a particular embodiment, the composition comprises valine, leucine, and isoleucine in approximately equivalent amounts (e.g., a 1:1:1 ratio). The amount of BCAA may be determined, for example, by weight or molar amount. While the BCAAs will often be present in equivalent amounts, the compositions of the instant invention may comprise excess amounts of one or two of the BCAAs. For example, the composition may comprise up to ten times, up to five times, or up to three times excess of one or two amino acids branched amino acid compared to another. For example, the composition may comprise excess valine.

Branched-chain amino acids are amino acids that have a fork or branch in the side chain. Branched chain amino acids include leucine, isoleucine and valine and precursors or analogs thereof. BCAAs may be administered in their free forms or salts thereof, as dipeptides, tripeptides, polypeptides (e.g., from about 2 to about 10 amino acids), and/or BCAA-rich proteins (e.g., proteins comprising at least 25%, at least 50%, or at least 75% or more BCAA content). In a particular embodiment, dipeptides, tripeptides and polypeptides may include two or more BCAAs. Where non-BCAAs are included in a dipeptide, tripeptide, or polypeptide, the non-BCAAs may be any amino acid, particularly alanine and/or glycine. Examples of dipeptides include, without limitation: isoleucyl-leucine, leucyl-alanine, alanyl-leucine, alanyl-isoleucine, alanyl-valine, glycyl-leucine, glycyl-isoleucine, and glycyl-valine.

Leucine precursors, such as pyruvate, and metabolites, such as β-hydroxy-β-methylbutyrate and α-ketoisocaproate, exhibit properties similar to those of leucine. These compounds may be administered as BCAAs as they are converted into the above-mentioned BCAA in vivo.

In a particular embodiment, the composition comprises independently from about 1 mg/ml to about 50 mg/ml, from about 5 mg/ml to about 25 mg/ml, from about 10 mg/ml to about 20 mg/ml, from about 13 mg/ml to about 20 mg/ml, or about 16 mg/ml of each of the three BCAA.

In a particular embodiment, at least about 40 g, at least about 50 g, at least about 60 g, at least about 70 g, or more of BCAAs are administered to the subject per day. In a particular embodiment, about 40 g to about 100 g of BCAAs are administered daily, particularly about 60 g to about 100 g, about 60 g to about 75 g, or about 60 g. Taking the subject's weight into account, at least about 40 g/70 kg, at least about 50 g/70 kg, at least about 60 g/70 kg, at least about 70 g/70 kg, or more of BCAAs are administered to the subject per day. In a particular embodiment, about 40 g/70 kg to about 100 g/70 kg of BCAAs are administered daily, particularly about 60 g/70 kg to about 100 g/70 kg, about 60 g/70 kg to about 75 g/70 kg, or about 60 g/70 kg. The BCAAs may be administered in more than one dosage to reach the daily goal (e.g., administered twice, three times, four times or more daily).

Compositions comprising large quantities of branched chain amino acids are not palatable to many subjects, particularly humans. Accordingly, compositions of the instant invention comprise at least one flavor masking agent, particularly a bitter taste receptor blocker. In a particular embodiment, the flavor masking agent is a salt of an organic acid. Examples of organic acids include, without limitation, gluconic acid and lactic acid. Suitable salts include, by way of example, calcium lactate, magnesium lactate, sodium lactate, calcium gluconate, magnesium gluconate, and sodium gluconate. In particular embodiment, the flavor masking agent is sodium gluconate.

In a particular embodiment, the flavor masking agent is present in the composition at about 5 g, at about 10 g, at about 15 g, at about 20 g, or more per 30 g of BCAAs. In a particular embodiment, the composition comprises at least about 50 mM, at least about 75 mM, at least about 100 mM, or more of the flavor masking agent. The compositions may also comprise at least one sweetener. Any natural or artificial sweetener may be used. Examples of sweeteners include, without limitation, sucrose, fructose, maltose, dextrose, sucralose, aspartame, saccharin, and the like. In a particular embodiment, the sweetener is sucralose.

In a particular embodiment, the sweetener is present in the composition at about 2 g, at about 5 g, at about 10 g, at about 15 g, or more per 30 g of BCAAs. In a particular embodiment, the composition comprises at least about 10 mM, at least about 20 mM, at least about 35 mM, or more of the sweetener.

The compositions may also comprise at least one flavoring agent. Any natural or synthetic flavor agent can be used in the present invention. One or more flavoring agents may be used to enhance the palatability of the compositions. The flavoring agent may be an emulsion, concentrate, aqueous- or oil-soluble liquid, dry powder, or a combination thereof. In a particular embodiment, the flavor agent is a concentrate or powder. In a particular embodiment, the flavoring agent is a fruit flavor. In a particular embodiment, the flavor agent is a concentrate powder (e.g., unsweetened tropical punch KoolAid® powder).

The methods of the instant invention may further comprise the administration of acetate. The compositions of the instant invention may also comprise acetate. Acetate may be administered to the subject as acetic acid or a pharmaceutically acceptable salt thereof, such as calcium acetate. In a particular embodiment, the acetate is delivered in a hydrophobic form, such as glyceryl triacetate (GTA; the acetate triester of glycerol). It has been shown that GTA can be used as a dietary supplement to increase acetate levels in the brain by over 15-fold within one hour of administration (Mathew et al. (2005) J. Pharmacol. Exp. Ther., 315:297-303). In a particular embodiment, about 0.5 mg/kg to about 100 mg/kg of GTA are administered daily, particularly about 0.5 mg/kg to about 10 mg/kg, about 2.5 mg/kg to about 7.5 mg/kg, or about 5 mg/kg.

In a particular embodiment, the composition of the instant invention comprises 10 g valine, 10 g leucine, 10 g isoleucine, 13 g sodium gluconate, 9 g sucralose, and a flavor concentrate in 630 ml of water. The composition may further comprise acetate (e.g., 175 mg GTA). The compositions of the instant invention may have the same ratio of components (±5%) in different volumes of water.

As used herein, "traumatic brain injury" or "TBI" refers to an acquired brain injury or a head injury, when a trauma causes damage to the brain. Trauma includes, e.g., post-head trauma, impact trauma, and other traumas to the head such as, for example, traumas caused by accidents and/or sports injuries, concussive injuries, penetrating head wounds, brain tumors, stroke, heart attack, meningitis, viral encephalitis, and other conditions that deprive the brain of oxygen. In a preferred embodiment, the trauma is an external, physical force.

The damage can be focal (confined to one area of the brain) or diffuse (involving more than one area of the brain). Clinically, traumatic brain injury can be rated as mild, moderate or severe based on TBI variables that include duration of loss of consciousness (LOC), Glasgow Coma Score (GCS; e.g., mild 13-15; moderate=9-12; severe=≤8) and post traumatic stress amnesia (see, e.g., Levin et al. (1979) J. Nervous Mental Dis., 167:675-84; Holm et al. (2005) J. Rehabil. Med., 37:137-41). In a particular embodiment, the TBI is mild or moderate.

In some embodiments, the traumatic brain injury can be chronic, where the brain is subject to repeated traumatic injury to the brain. Generally, chronic traumatic brain injury is typically a mild to moderate form of closed brain injury repeatedly suffered by a subject (e.g., athlete), resulting in increased incidence of impaired motor, cognitive, and/or behavioral impairments months to years following the traumatic brain injuring events. Individuals subjected to such chronic brain injury appear to have increased susceptibility to certain neurological disorders, such as Alzheimer's disease, chronic traumatic encephalopathy (CTE), and/or Parkinson's Disease.

In some embodiments, the traumatic brain injury can result from a closed head injury. The closed head injury may be transient or prolonged. A "closed head injury" refers to a brain injury when the head suddenly and violently hits an object but the object does not break through the skull. In some embodiments, the closed head injury is a concussion or contusion. A concussion is a mild form of traumatic brain injury resulting in temporary impairment of neurological function which quickly resolves by itself, and where there are generally no gross structural changes to the brain as the result of the condition. A contusion is a distinct area of swollen brain tissue mixed with blood released from broken blood vessels. A contusion can also occur in response to shaking of the brain back and forth within the confines of the skull, an injury referred to as "contrecoup." As used herein, a closed head injury refers to an injury due to an external, physical trauma and does not encompass brain injury resulting from "internal" forces such as ischemia/reperfusion and stroke.

Sleep disorders are a common pathology associated with traumatic brain injury and can significantly impair cognitive rehabilitation. Hereinbelow, a well-established mouse model of mild brain injury (i.e., lateral fluid percussion injury) was used which recapitulates the chronic sleep disturbances seen in the human condition. Brain-injured mice demonstrate a persistent inability to maintain wakefulness and severe sleep-wake fragmentation. EEG power spectral analyses show a shift to slower peak theta frequencies. When placed in a novel environment, injured mice have a shorter latency and higher pressure to sleep. TBI-induced sleep disturbance resembles the narcoleptic phenotype, and the neuropeptide orexin (also known as hypocretin) has been implicated in both disorders. Brain-injured mice show significantly less activation of orexin neurons in response to sustained wakefulness. To ameliorate TBI-induced pathology including orexin neuron activation, mice were given a dietary supplement consisting of branched chain amino acids (BCAA) which are precursors for de novo glutamate synthesis in the brain. BCAA therapy reinstated activation of orexin neurons in injured mice and restored wakefulness by increasing wake time, consolidating sleep and wake bouts, and increasing arousal during wake challenges. The data identify novel mechanisms underlying sleep disturbances in a model of mild TBI and indicate that BCAA intervention, likely acting in part through orexin, can normalize injury-induced sleep disturbances and, thus, facilitate cognitive rehabilitation.

In accordance with another aspect of the instant invention, methods for treating, preventing, and/or inhibiting a sleep disorder associated with a traumatic brain injury are provided. The methods comprise administering branched chain amino acids to a subject who has sustained a traumatic brain injury. The sleep disorders associated with a traumatic brain injury are generally known in the art (see, e.g., Kushner, D. (1998) Arch. Intern. Med., 158:1617-24; Parsons et al. (1982) Nurs. Res., 31:260-264; Viola-Saltzman et al. (2012) Neurol. Clin., 30:1299-312; Castriotta et al. (2011) CNS Drugs 25:175-85). In a particular embodiment, the sleep disorder is a problem/disruption with the onset and/or maintenance of sleep (e.g., sleep-wake fragmentation). Examples of sleep disorders associated with a traumatic brain injury include, without limitation, insomnia (e.g., difficulty with falling asleep and/or staying asleep), fatigue, drowsiness, sleep apnea, narcolepsy, and/or sleepiness (e.g., excessive daytime sleepiness). Sleep disorders may be diagnosed any means such as a sleep study, polysomnography, multiple sleep latency testing, maintenance of wakefulness testing, and/or actigraphy. The methods of the instant invention may further comprise examining/diagnosing the patient for a sleep disorder after the traumatic brain injury and prior to treatment. The methods may also further comprise examining/diagnosing the patient for a sleep disorder after the traumatic brain injury and after treatment. Treatment with the BCAAs may be stopped once the sleep disorder has been resolved.

As stated above, the methods comprise administering branched chain amino acids to a subject who has sustained a traumatic brain injury. The BCAAs may be administered before, during, and/or after the traumatic brain injury. For example, the subject may be administered the BCAAs prior to sustaining a traumatic brain injury (e.g., prior to participating in an activity with an increased likelihood of sustaining a traumatic brain injury such as participating in a contact sport (e.g., hockey, football, rugby, etc.). The subject may be administered BCAA therapy after sustaining the injury. In a particular embodiment, the subject is administered BCAA therapy (e.g., daily) prior to sleep (e.g., within about 30 minutes or about 1 hour).

The BCAAs may be administered to the subject by anvy means. In a particular embodiment, the BCAAs are administered in a liquid consumable (e.g., the palatable/drinkable compositions described hereinabove). The BCAAs administered to the subject may include one, two, or all three of valine, leucine, and isoleucine. In a particular embodiment, valine, leucine, and isoleucine are administered in approximately equivalent amounts (e.g., a 1:1:1 ratio). The amount of BCAA may be determined, for example, by weight or molar amount. While the BCAAs will often be administered in equivalent amounts, excess amounts of one or two of the BCAAs may be administered. For example, up to ten times, up to five times, or up to three times excess of one or two amino acids compared to another may be administered. For example, the excess valine compared to leucine and/or isoleucine may be administered.

As explained hereinabove, the BCAAs may be administered in their free forms or salts thereof, as dipeptides, tripeptides, polypeptides (e.g., from about 2 to about 10 amino acids), and/or BCAA-rich proteins (e.g., proteins comprising at least 25%, at least 50%, or at least 75% or more BCAA content). The BCAAs may be isolated. In a particular embodiment, dipeptides, tripeptides and polypeptides may include two or more BCAAs. Where non-BCAAs are included in a dipeptide, tripeptide, or polypeptide, the non-BCAAs may be any amino acid, particularly alanine and/or glycine. Examples of dipeptides include, without limitation: isoleucyl-leucine, leucyl-alanine, alanyl-leucine, alanyl-isoleucine, alanyl-valine, glycyl-leucine, glycyl-isoleucine, and glycyl-valine.

Leucine precursors, such as pyruvate, and metabolites, such as β-hydroxy-β-methylbutyrate and α-ketoisocaproate, exhibit properties similar to those of leucine. These compounds may be administered as BCAAs as they are converted into the above-mentioned BCAA in vivo.

In a particular embodiment, at least about 40 g, at least about 50 g, at least about 60 g, at least about 70 g, or more of BCAAs are administered to the subject per day. In a particular embodiment, about 40 g to about 100 g of BCAAs are administered daily, particularly about 60 g to about 100 g, about 60 g to about 75 g, or about 60 g. Taking the subject's weight into account, at least about 40 g/70 kg, at least about 50 g/70 kg, at least about 60 g/70 kg, at least about 70 g/70 kg, or more of BCAAs are administered to the subject per day. In a particular embodiment, about 40 g/70 kg to about 100 g/70 kg of BCAAs are administered daily, particularly about 60 g/70 kg to about 100 g/70 kg, about 60 g/70 kg to about 75 g/70 kg, or about 60 g/70 kg. The BCAAs may be administered in more than one dosage to reach the daily goal (e.g., administered twice, three times, four times or more daily).

In a particular embodiment, the BCAAs are administered immediately or soon after the traumatic brain injury event. For example, the BCAAs are administered at least within a month of injury, within two weeks of injury, within about the first 2, 3, 4 or 7 days after injury, within about the first day after injury, or within about the first hour after injury. In a particular embodiment, the BCAAs are administered within about the first 2 days of the injury. The BCAAs may be administered continually (e.g., every day) after the injury for at least one week, particularly at least two weeks, at least three weeks, at least four weeks or more.

I. Definitions

The singular forms "a," "an," and "the" include plural referents unless the context clearly dictates otherwise.

As used herein, "cognitive impairment" refers to an acquired deficit in at least one of the following: memory function, problem solving, orientation, and abstraction. The deficiency typically impinges on an individual's ability to function independently.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g., chromatographic methods, agarose or polyacrylamide gel electrophoresis, HPLC analysis, and the like).

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, preservative, antioxidant, solubilizer, emulsifier, adjuvant, excipient, bulking substances, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

The term "pathology" refers to any deviation from a healthy or normal condition, such as a disease, disorder, syndrome, or any abnormal medical condition.

The term "treat" as used herein refers to any type of treatment that imparts a benefit to a patient suffering from an injury (e.g., TBI), including improvement in the condition of the patient (e.g., in one or more symptoms), delay in the progression of the condition, etc.

As used herein, the term "prevent" refers to the prophylactic treatment of a subject who is at risk of developing a condition and/or sustaining an injury (e.g., TBI) resulting in a decrease in the probability that the subject will develop conditions associated with the injury.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated traumatic brain injury in a patient.

As used herein, the term "subject" refers to an animal, particularly a mammal, particularly a human.

II. Administration

The agents of the instant invention used to treatment, inhibition, reduction, and/or prevention of the symptoms and/or pathology associated with traumatic brain injury (e.g., cognitive impairment, increased seizure rate) may be administered to a patient orally, such as a liquid consumable or pharmaceutical preparation. The term "patient" as used herein refers to human or animal subjects.

The instant invention encompasses compositions comprising BCAAs and, optionally, at least one pharmaceutically acceptable carrier or other component as described hereinabove. As used herein, "pharmaceutically acceptable carrier" includes any and all solvents, dispersion media and the like which may be appropriate for the desired route of administration of the pharmaceutical preparation. The use of such media for pharmaceutically active substances is known in the art. Except insofar as any conventional media or agent is incompatible with the molecules to be administered, its use in the pharmaceutical preparation is contemplated.

The compositions comprising at least one of the agents of the instant invention may be conveniently formulated for administration with a pharmaceutically acceptable carrier. Solubility limits of the agents within the particular pharmaceutically acceptable carrier may be easily determined by one skilled in the art.

Compositions of the instant invention may be administered orally. The pharmaceutical composition of the present invention can be prepared, for example, in liquid form (including concentrated liquid form requiring dilution (e.g., with water) prior to consumption), or can be in dried powder form (e.g., lyophilized for later reconstitution (e.g., with water). Dosage forms for oral administration include, without limitation, tablets (e.g., coated and uncoated, chewable), sustained release capsules, gelatin capsules (e.g., soft or hard), solutions, drinks, concentrates, emulsions, suspensions, syrups, elixirs, and powders/granules (e.g., reconstitutable or dispersible).

The BCAAs of the instant invention may also be administered nasally (e.g., via nasal pump, nasal spray, nasal drops, etc.). For example, a composition comprising the BCAAs can be administered as an aerosol formulation which contains the BCAAs in dissolved, suspended or emulsified form in a propellant or a mixture of solvent and propellant. The aerosolized formulation is then administered through the respiratory system or nasal passages. An aerosol formulation used for nasal administration may be an aqueous solution designed to be administered to the nasal passages in drops or sprays. The nasal solutions may also be administered without propellant—e.g., via nasal drops, spray or mist (e.g., an atomized spray). Nasal solutions are generally prepared to be similar to nasal secretions and are generally isotonic and slightly buffered to maintain a pH of about 5.5 to about 6.5, although pH values outside of this range can additionally be used (e.g., a pH of about 5 to about 8). Antimicrobial agents or preservatives can also be included in the formulation.

Pharmaceutical compositions containing agents of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., oral.

The compounds/compositions of the instant invention may also be encapsulated within a protective material (e.g., one that is polymeric in nature or one which is lipid-based (e.g., liposomes or micelles)). The polymeric drug delivery system may be colloidal or non-colloidal in nature and may be composed of biodegradable or non-biodegradable polymeric materials. Colloidal polymeric encapsulation structures include, without limitation, microparticles, microspheres, nanoparticles, and nanospheres, block copolymer micelles, and the like. In a particular embodiment, the compounds and/or compositions of the instant invention may be formulated within a nanomaterial carrier. Suitable nanomaterial carriers are known to those skilled in the art. In a particular embodiment, the nanomaterial carrier is a nanoparticle or a nanosphere. Nanoparticles or nanospheres typically range from about 1 to 1,000 nanometers (nm), particularly from about 50 to 300 nm. The term "nanosphere" refers to a type of nanoparticle that is approximately spherical in shape. The nanosphere may have a hollow core within which one or more compounds can be placed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of compositions of the instant invention may be determined by evaluating the toxicity of the molecules or cells in animal models. Various concentrations of the agents in pharmaceutical preparations may be administered to mice, and the minimal and maximal dosages may be determined based on the beneficial results and side effects observed as a result of the treatment. Appropriate dosage unit may also be determined by assessing the efficacy of the treatment in combination with other standard drugs. The dosage units may be determined individually or in combination with each treatment according to the effect detected.

The compositions of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

In a particular embodiment, the composition(s) of the instant invention are administered immediately or soon after the traumatic brain injury event. For example, the pharmaceutical preparation is administered at least within a month of injury, within two weeks of injury, within about the first 7 days after injury, within about the first day after injury, within about the first hour after injury.

The compositions of the instant invention may be administered continually (e.g., every day) after the injury for at least one week, particularly at least two weeks, at least three weeks, at least four weeks or more.

In general, the compositions of the instant invention may contain other components in amounts that do not detract from the preparation of effective safe formulations. The compositions of the instant invention may further comprise at least one preservative, stabilizer, carriers, excipients, and/or antibiotic. The compositions and methods of the instant invention may also be combined with other compositions and methods for the treatment of the symptoms and/or pathology of a traumatic brain injury.

The following examples describe illustrative methods of practicing the instant invention and are not intended to limit the scope of the invention in any way.

EXAMPLE 1

Lateral fluid percussion injury (LFPI; McIntosh et al. (1989) Neurosci., 28:233-244) results in changes in network excitability in the mouse hippocampus, notably a decrease in net synaptic efficacy excitability in area CA1 and an increase in net synaptic efficacy in the dentate gyms. Dietary supplementation with branched chain amino acids (BCAAs) leucine, isoleucine, and valine initiated 48 hours after LFPI and maintained for 5 days restores net synaptic efficacy in the mouse hippocampus and re-instates hippocampal dependent cognitive function at 7 days following LFPI (Cole et al. (2010) PNAS 107:366-371).

Materials and Methods

Fluid percussion injury (FPI): After craniectomy, a Luer-loc needle hub (3 mm inner diameter) was secured above the skull opening. On the next day, the hub was filled with saline and connected via high-pressure tubing to the FPI device. The injury was induced by a brief pulse of saline onto the intact dura. Sham animals received all of the above except the fluid pulse.

BCAA diet: Two days after FPI, animals received the BCAA diet via water bottle or by gavage feeding. Animals that received the water bottles (100 mM) were able to consume the diet ad libitum. Animals that received the gavage were fed (60 g/70 kg) every day. Animals received an LFPI and two days later BCAA diet was initiated for a duration of 2, 3, 4, 5, or 10 days. Following diet administration, animals were tested for cognitive improvement via conditioned-fear response. An additional group received the diet for 5 days and subsequently had the diet removed for 5 days prior to undergoing behavioral testing.

Behavior: Animals were tested for anterograde cognitive recovery using conditioned fear response (CFR) at 4, 5, 6, 7, or 12 days after injury. On day 1, animals were placed in the CFR box for a total of 3 minutes. At minute 2:32, animals received a 2-second, 1.07 mA shock and remained in the box for 30 additional seconds. The following day, animals are placed in the CFR box and observed every 5 seconds for a total of 5 minutes. A total of 60 observations were used to determine freezing percentage. Freezing percentages were calculated based on the number of times over a 5 minute period that the animal froze.

Results

To determine the concentration and the duration of BCAA supplementation necessary to maximally enhance cognitive reinstatement, cognitive function was evaluated using conditioned fear response (CFR). Briefly, mice were administered an LFPI and placed on a 100 mM BCAA dietary supplement for 2, 3, 4, 5, or 10 days. As seen in FIG. 1, the length of time of administration correlated with an increase efficacy in CFR.

As seen in FIG. 2, the administration of BCAAs for 10 days following FPI improves performance in CFR when compared to injured mice without BCAAs. A third group of mice were placed on the diet for 5 days and then taken off the diet for 5 days. When compared to injured mice that received the diet for 10 days, the 5 day on/5 day off animals did not show significant improvements in cognition as assayed with CFR.

As seen in FIG. 3, decreasing the original BCAA concentration of 100 mM to a concentration of 50 mM was not efficacious in restoring cognitive ability in FPI mice when treating for 5 days.

FIG. 4 shows an improved efficacy as a result of a dose specific treatment with BCAAs for 3 days and 5 days compared to injured alone. Specifically, animals received FPI and two days later received the BCAA diet via gavage feeding at a dose of 60 mg/70 kg/day. Following diet administration for 3 or 5 days, animals were tested for cognitive improvement via conditioned-fear response. Animals receiving gavage feeding showed improved performance when compared to injured alone.

These results indicate that brain injured animals need to remain on the diet to retain restorations in cognitive function. Furthermore, dietary intervention for five days is insufficient to permanently reverse alterations in glial-neuronal function caused by LFPI indicating clinical therapies for TBI may require a protracted time course.

Table 1 provides the average freezing percentage and standard deviation by condition. The data demonstrate that by 10 days animals are freezing at similar percentages as sham animals. Animals on the diet show improved performance when compared to animals from the same time point that did not undergo dietary therapy.

TABLE 1

The average incidence of freezing over a 5-minute observation period and standard deviations.

|  | With Treatment | Without Treatment |
| --- | --- | --- |
| Sham | — | 38.81 ± 11.77 |
| 2-Day | 21.46 ± 5.38 | 11.00 ± 4.01 |
| 3-day | 25.24 ± 9.20 | 18.75 ± 8.90 |
| 4-Day | 25.63 ± 9.76 | 18.10 ± 6.83 |
| 5-Day | 32.89 ± 12.57 | 21.46 ± 10.63 |
| 10-Day | 40.67 ± 16.77 | 25.97 ± 10.60 |
| 5-Day (50 mM) | 17.33 ± 10.11 | — |

The above results show that the administration of BCAAs via water bottle or gavage feeding to FPI animals improves behavioral performance in CFR when compared to injured animals at the same time point that did not undergo BCAA dietary therapy. It is necessary for animals to continually receive the diet for at least 10 days in order to show performance similar to sham animals.

EXAMPLE 2

A fluid percussion injury assay was performed. Briefly, a craniotomy was performed on anesthetized mice using a 3 mm trephine and a Luer-Hoc needle hub attached to the skull and capped. The following day, a fluid percussion injury device was employed to deliver a pulse of saline through the hub at a pressure between 1.4-2.14 atm, producing a mild to moderate percussion injury. Sham animals received all anesthesia and surgical procedures except for the fluid pulse.

Mice were allowed to recover for one day. Mice were then treated with 5 mg/kg of glyceryl triacetate (GTA) via oral gavage for 5 days. The conditioned fear response (CFR) assay was performed on day 7. As seen in FIG. 5, mice treated with GTA after injury showed a similar fear response to sham animals and a statistically superior (P<0.05) response to those mice receiving the brain injury without treatment.

EXAMPLE 3

Recent data from the Centers for Disease Control estimates that traumatic brain injury (TBI) afflicts nearly 2 million people in the nation annually and is a major cause of disability in all age groups. Even mild TBI or concussion can have chronic neurological sequelae, including cognitive, motor, and sleep problems (McCrea et al. (2002) Neurosurgery 50:1032-1040; Giza et al. (2001) J. Athl. Train., 36:228-235). Sleep disorders are highly prevalent in patients with TBI (Castriotta et al. (2010) CNS Drugs 25:175-185; Castriotta et al. (2007) J. Clin. Sleep Med., 3:349-356). Sleep disturbances have been reported in up to 72% of patients with TBI (including mild TBI) up to three years post-injury (Baumann et al. (2007) Brain 130:1873-1883; Kempf et al. (2010) J. Neurol. Neurosurg. Psychiatry 81:1402-1405). TBI patients with sleep disturbances have longer inpatient hospital stays, a higher cost of rehabilitation, and a higher rate of functional disability (Makley et al. (2008) Neurorehabil. Neural Repair 22:341-347; Makley et al. (2009) Neurorehabil. Neural Repair 23:320-326). Moreover, sleep disruption is known to impair memory formation and may exacerbate cognitive deficits in TBI (McDermott et al. (2003) J. Neurosci., 23:9687-9695; Ruskin et al. (2004) Eur. J. Neurosci., 19:3121-3124). At present, there are no proven therapies to mitigate or prevent the neurocognitive and neurobehavioral consequences of TBI (Castriotta et al. (2009) J. Clin. Sleep Med., 5:137-144). Therefore, there is an imminent need to understand the neural mechanisms underlying brain injury and chronic sleep disturbances and a need for alternative therapeutic options.

Seventy-five percent of reported TBI cases are mild in nature (i.e., concussion), and sleep disturbances have been reported in 47% of 639 patients presenting to a minor head injury clinic (Haboubi et al. (2001) Disabil. Rehabil., 23:635-638). A widely-accepted, commonly used mouse model of mild TBI is the lateral fluid percussion injury (FPI) model (Dixon et al. (1987) J. Neurosurg., 67:110-119; McIntosh et al. (1989) Neuroscience 28:233-244). This experimental method provides a highly-reproducible, closed head injury that recapitulates many key features of human TBI including memory deficits, gliosis, and electrophysiological perturbation (Dixon et al. (1987) J. Neurosurg., 67:110-119; McIntosh et al. (1989) Neuroscience 28:233-244). A variety of assays have been used to demonstrate that this animal model recapitulates chronic sleep disturbances after FPI. For example, long term activity monitoring using a previously validated locomotor beam break assay was used (Pack et al. (2007) Physiol. Genomics 28:232-238). In order to further investigate changes in activity profiles, EEG/EMG recordings in freely behaving mice were performed, which allowed assessment of non-rapid-eye-movement (NREM) sleep, rapid-eye-movement (REM) sleep and wake states, and power spectral analyses.

To investigate the neural mechanisms underlying injury-induced sleep disturbances, the neuropeptide orexin was examined, which is involved in maintaining wakefulness (Chemelli et al. (1999) Cell 98:437-451). Cerebrospinal fluid (CSF) orexin levels and hypothalamic orexin neuron numbers are significantly decreased in both narcolepsy (a human sleep disorder characterized by excessive daytime sleepiness and sleep fragmentation) as well as after human TBI (Chemelli et al. (1999) Cell 98:437-451; Baumann et al. (2009) Ann. Neurol., 66:555-559; Baumann et al. (2005) Neurology 65:147-149; Krahn et al. (2002) Sleep 25:733-736). Therefore, mild TBI may cause dysfunction of the orexin system.

Injury-induced deficits in the orexin system may be reversed with dietary branched chain amino acid (BCAA) supplementation. BCAA serve as precursors for de novo glutamate and subsequent GABA synthesis in the brain. It has been shown that FPI induces a secondary cascade of injury that affects the balance of excitation to inhibition (E-I) and causes regional shifts in network excitability in the hippocampus, all of which are restored with BCAA therapy (Cole et al. (2010) Proc. Natl. Acad. Sci., 107:366-371; Witgen et al. (2005) Neuroscience 133:1-15). In addition, dietary amino acids have been shown to act directly on orexin neurons to modulate membrane excitability (Karnani et al. (2012) Neuron 72:616-629). Herein, mice were given BCAA supplementation in their drinking water and reinstated both orexin neuron activation and injury-induced sleep disturbances, indicating that BCAA restore wakefulness in part by activating orexigenic (hypocretinergic) neurons.

The data presented herein identify novel mechanisms underlying sleep disturbances in a model of mild TBI and show for the first time that BCAA intervention ameliorates injury-induced sleep disturbances, thereby identifying a therapy for the cognitive and neurobehavioral sequelae from mild TBI.

Methods

Animals

All experiments were performed on 5-7 week old, 20-25 g, male C57BL/J6 mice (Jackson Laboratory). The animals were housed in an insulated and soundproof recording room that was maintained at an ambient temperature of 23±1° C. with a relative humidity of 25±5% and that was on an automatically controlled 12-h light/12-h dark cycle (light on at 07:00 hours, illumination intensity lux). The animals had free access to food and water. Every effort was made to minimize the number of animals used and any pain and discomfort experienced by the subjects. Animal experiments were performed in accordance with the guidelines published in the National Institutes of Health Guide for the Care and Use of Laboratory Animals and were approved by the University of Pennsylvania and Children's Hospital of Philadelphia Animal Care and Use Committee in accordance with international guidelines on the ethical use of animals.

Mouse Fluid Percussion Brain Injury

Mice were divided into two groups: TBI (surgery and fluid percussion injury) and Sham. The fluid percussion brain injury (FPI) protocol was carried out over 2 days as previously described (McIntosh et al. (1989) Neuroscience 28:233-244; Cole et al. (2010) Proc. Natl. Acad. Sci., 107:366-371). On the first day, the animal was anesthetized using a combination of ketamine (100 mg/kg) and xylazine (10 mg/kg) and placed in a mouse stereotactic frame (Stoelting). The scalp was incised and reflected. The following was conducted under 0.7-3.5× magnification: A craniectomy was performed with a trephine (3-mm outer diameter) over the right parietal area between bregma and lambda, just medial to the sagittal suture and lateral to the lateral cranial ridge. The dura remained intact throughout the craniotomy procedure. A rigid Luer-lock needle hub (3-mm inside diameter) was secured to the skull over the opening with Loctite® adhesive and subsequently cyanoacrylate plus dental acrylic. The skull sutures were sealed with the cyanoacrylate during this process to ensure that the fluid bolus from the injury remained within the cranial cavity. The Luer-lock needle hub was filled with isotonic sterile saline and the hub was capped. The mouse was then placed on a heating pad and returned to the home cage once ambulatory. On the second day, the animal was briefly placed under isoflurane anesthesia (500 mL/min) via nose cone, and respiration was visually monitored. When the animal was breathing once per 2 seconds, the nose cone was removed, the cap over the hub removed, and dural integrity visually confirmed. The hub was topped off with isotonic sterile saline, and a 32-cm section of high-pressure tubing extending from the FPI device attached to the Luer-lock fitting of the hub (Department of Biomedical Engineering, Virginia Commonwealth University, Richmond, Va.). The animal was then placed on its left side and observed. Once normal breathing resumed and just as the animal regained its toe pinch withdrawal reflex, a 20-ms pulse of saline onto the dura was delivered. A pressure gauge attached to an oscilloscope was used to ensure delivered pressures between 1.4 and 2.1 atmospheres, which have been previously shown to generate a mild brain injury. Immediately after injury, the hub was removed from the skull and the animal was placed in a supine position. The animal was then reanesthetized with isoflurane for scalp closure. Sham animals received all of the above, with the exception of the fluid pulse. The animal was returned to a heating pad until ambulatory and then returned to the home cage.

Assessment of Activity and Inactivity: Infrared Beam Breaks

The activity monitoring timeline is detailed in FIG. 6A. Activity/inactivity was determined using the Accuscan monitoring system (Omnitech Electronics, Inc.) and Fusion 4.0 software collection system. Following FPI or sham surgery, mice were individually housed in their home cages within the Accuscan monitoring system for 30 consecutive days (n=18 FPI, n=12 sham). The Accuscan system consists of infrared beam that are 1 inch apart on the horizontal plane providing a high-resolution grid covering cage bottom. Data acquisition software provides counts of beam breaks by the mouse in 10 second epochs. The mouse was considered inactive if there were no beam breaks in four consecutive 10 second epochs, in accordance with an algorithm developed to estimate sleep and wakefulness (Pack et al. (2007) Physiol. Genomics 28:232-238).

EEG/EMG Assessment of Sleep and Wakefulness

To assess sleep and wakefulness, mice were surgically implanted with EEG/EMG electrodes as previously described, with slight modifications for the craniotomy from FPI (Pack et al. (2007) Physiol. Genomics 28:232-238). Briefly, animals were anesthetized by injection of ketamine (100 mg/kg) and xylazine (10 mg/kg). The skull was exposed and 3 small holes prepared for placement of 3 silver ball EEG electrodes, two frontal and one left parietal (anteroposterior, +1.0 mm; mediolateral, +1.5 mm from bregma, and anteroposterior, −2.0 mm; mediolateral −2.0 mm) according to the atlas of Franklin and Paxinos (Paxinos, G. (2004). The mouse brain in stereotaxic coordinates: Gulf Professional Publishing). Two insulated stainless steel EMG electrodes bared at the tips were buried on the surface of dorsal neck muscles. All leads from the electrodes were connected to a plastic socket connector (Plastics One), which was fixed to the skull with dental acrylate. Following surgery, animals were allowed to recover for 5 days before any studies were performed. EEG and EMG signals were amplified using the Neurodata amplifier system (model M15, Astro-Med Inc.). Signals were amplified (20,000×) and conditioned with neuroamplifiers/filters (model 15A94, Grass). Settings for EEG signals were a low cut frequency (−6 dB) of 0.1 Hz and a high cut frequency (−6 dB) of 100 Hz. Samples were digitized at 256 Hz samples/second/channel. All data were acquired using Grass Gamma software (Natus).

Branched Chain Amino Acid (BCAA) Administration

Two days after FPI procedure, a subset of mice was randomly assigned to receive either BCAA supplemented water, or untreated tap water (control). BCAA supplementation consisted of a combination of L-Leucine, L-isoleucine, and L-Valine at 100 mM each (obtained individually from Sigma-Aldrich) (Cole et al. (2010) Proc. Natl. Acad. Sci., 107:366-371). The amount of drinking water remaining in the bottle was measured each day, and fresh BCAA or control water replaced each week. Mice drank on average 3-5 mL of solution per day and it has been shown that BCAA do not affect body weight (Cole et al. (2010) Proc. Natl. Acad. Sci., 107:366-371).

Recording Timeline and Behavior Testing

The EEG/EMG recording timeline is shown in FIG. 7. Mice were connected to lightweight recording cables in individual cages (n=7 Sham, n=6 TBI, n=6 TBI+BCAA). Sleep recordings were initiated after 24 hours of acclimation to the cables. Ability to move freely within the entire cage and stand on hind limbs to explore the top of the cage was confirmed in all mice studied. Baseline sleep was recorded on the first, second and fifth days to ensure stable sleep/wake activity across days. At the start of the dark phase (7:00 pm) on recording day 3, mice were exposed to a novel environment without direct handling by adding new bedding and a nestlet to their home cages. EEG/EMG signals were recorded and analyzed from 7:00 to 9:00 pm for response to a novel environment. On recording day 4, mice were sleep deprived using gentle handling for 3 hours, from 10:00 am to 1:00 pm, which is a time of heightened sleep. Gentle handling was accomplished by providing the mice with novel materials (bedding, nestlets, pieces of paper towels, aluminum foil, and saran wrap) and occasionally stroking the mice with a soft paintbrush as described (Naidoo et al. (2011) Aging Cell, 10:640-649). During this enforced wakefulness, wake was electrographically confirmed during the entire 3 hour period. Subsequently, recovery sleep for the next three hours was recorded and analyzed for wake probability and delta power as described below in Data Analysis.

Data Analysis: Baseline EEG/EMG Scoring

Polygraphic records were scored offline by an experienced scorer for non-rapid-eye movement (NREM) and rapid-eye-movement (REM) sleep and wakefulness (W) in 4 second epochs across a 24 hour baseline (12 hour light-dark cycle from 7:00 am to 7:00 pm). Data collected using the Grass Gamma software were converted to European Data Format and automatically scored using the SleepSign analysis package according to standard criteria (Kissei Comtec). Automatically scored epochs were then visually inspected for artifact and manually removed (<0.5% of all epochs). As a final step, defined sleep-wake stages were examined and corrected if necessary. Over a baseline period of 24 hours consisting of exactly 21,600 epochs per mouse, total minutes of Wake, NREM, and REM sleep, the average length of each sleep and wake bout, and the characteristics of the transitions within and between sleep and wake states were quantified.

Data Analysis: Baseline Power Spectral Analysis

Scored polygraphic signals underwent Fast Fourier Transform (FFT) using SleepSign for power spectral analysis of each 0.25 Hz frequency bin from 0 to 128 Hz in total for each sleep stage (NR, R, and W). The data were then aggregated using R for power density within particular EEG frequency bands: Delta (1-4 Hz), theta (5-8 Hz), alpha (9-13 Hz), and beta (14-30 Hz), total gamma (31-128 Hz), slow gamma (35-55 Hz) and total power (1-128 Hz). The EEG power density for each epoch was normalized by the total power averaged from all epochs and summed within each frequency bin for each sleep stage. Epochs containing artifacts were eliminated from power spectral analysis. Theta peak frequency was calculated by identifying the frequency between 5 and 8 Hz which had the greatest power density for each individual mouse, and then averaging this value within groups.

Data Analysis: Novel Environment

Polygraphic records over the analysis period for Novel Environment were extracted from 7:00 to 9:00 pm on recording day 3, and scored in the same manner as detailed above. The latency to the first sleep period, defined as 3 consecutive NREM or REM epochs in any combination, was quantified for each mouse. The chronological plot of percentage wakefulness was calculated by tabulating the total number of wake epochs within consecutive 5 minute bins and expressing this as a percentage of total epochs, plotted over 120 minutes.

Data Analysis: Recovery Sleep

Polygraphic signals were extracted from the Recovery Sleep period occurring immediately after a 3 hour period of enforced wakefulness, from 1:00 pm to 7:00 pm on recording day 4. The epochs were scored as above and analyzed for total NREM time and average NREM bout length. Delta power was calculated by quantifying the average NREM power for each hour immediately following sleep deprivation from 1:00 pm to 7:00 pm, and then normalized by dividing by the baseline NREM delta power for each individual mouse. The baseline NREM delta power was calculated by averaging values over the last four hours of Lights On (3:00 pm to 7:00 pm) during baseline day 3, where values are presumably at their zenith (Franken et al. (2001) J. Neurosci., 21:2610-2621). The chronological plot of percentage wakefulness was calculated by tabulating the total number of wake epochs within consecutive 5 minute bins and expressing this as a percentage of total epochs, plotted over 3 hours.

Immunohistochemistry

Immunohistochemistry was used to characterize the waking c-fos response in orexin neurons, an immediate early gene marker of recent neural activation. Mice were perfused with 4% paraformaldehyde, and brains were post-fixed then cryopreserved in sucrose. Cryostat sections were collected at 40 um thickness in a 1:6 series. Sections containing the lateral hypothalamus underwent double-labeling for orexin and c-Fos as described (Naidoo et al. (2011) Aging Cell 10:640-649). Briefly, sections were incubated in goat polyclonal anti-Orexin-A antibody (Santa Cruz) at 1:1000 concentration and rabbit polyclonal anti-c-Fos antibody (Calbiochem) at 1:6000 concentration. Orexin-A was visualized with an anti-goat Alexa Fluor® 594 (red) secondary antibody at 1:200, and c-Fos was visualized with an anti-rabbit Alexa Fluor® 488 (green) secondary antibody at 1:200 (Molecular Probes). For Vesicular Glutamate Transporter 1 (VGLUT1) and Orexin-A double-labeling, the protocol was the same with the exception of using rat polyclonal anti-VGLUT1 antibody (Synaptic Systems) at 1:2000 concentration. Sections were mounted onto microscope slides and analyzed for cell counting using an epifluorescent microscope (Leica) at 10× and 40× magnification as previously described (Naidoo et al. (2011) Aging Cell 10:640-649).

Cell Counting

All immunopositive orexin-A neurons with visible nuclei in four rostral-caudal sections across bilateral nuclei for each mouse were analyzed (n=5 mice per group). Cells were scored as c-Fos positive if c-Fos labeling in the nucleus was more intense than background using Image J analysis software (NIH) as previously described (Naidoo et al. (2011) Aging Cell 10:640-649). Two scorers, one of whom was blinded to conditions, independently counted orexin neuron numbers and c-Fos labeling with >90% agreement. For each mouse, greater than 150 neurons per region were examined.

Statistical Procedures

Statistical calculations and analyses were performed using R (Version 2.15.2, The R Foundation of Statistical Computing) (Team, R.C. (2012) R: A language and environment for statistical computing. Vienna, Austria: R Foundation for Statistical Computing). Where appropriate, all data were analyzed using either two-tailed Student's t-tests or a one-way ANOVA followed by Dunnett's post-hoc tests if the F values reached statistical significance. Statistical significance was defined at the $p<0.05$ confidence level when comparing different treatment groups. All data are presented as group means±SEM.

Results

Activity Monitoring: Decreased and Fragmented Activity

A widely-accepted, commonly used mouse model of mild TBI is the lateral fluid percussion injury (FPI) model. This experimental method provides a highly-reproducible, closed head injury that recapitulates many key features of human TBI including memory deficits, gliosis, and electrophysiological perturbation (Dixon et al. (1987) J. Neurosurg., 67:110; McIntosh et al. (1989) Neuroscience 28:233).

Mice randomized to either FPI or Sham surgery underwent extensive locomotor activity monitoring from 3 to 34 days. The experimental timeline denoting the pre-determined time blocks is shown in FIG. 6A, and consists of the immediate post-operative period (days 0-4), acute (days 5-14), subacute (days 15-24) and chronic (days 25-34) periods following injury or sham surgery. Activity patterns were analyzed for each of the time blocks. A previously established algorithm was applied in which 40 seconds of continuous inactivity was shown to be highly predictive of sleep (Pack et al. (2007) Physiol. Genomics 28:232-238). Therefore, an inactive bout was counted only when mice remained still for greater than 40 continuous seconds.

During the dark phase (7:00 pm to 7:00 am), when mice are typically more active, injured mice were significantly less active compared to Sham controls during the subacute and chronic phases (FIG. 6B). The average length of time spent continuously inactive, or "Inactive Bout Length," did not significantly differ between groups (FIG. 6C). However, the average length of time spent continuously active, or "Active Bout Length," was significantly shorter in TBI mice compared to controls (FIG. 6D). This indicates that mild TBI decreases total activity by causing shorter bouts of continuous activity.

TBI and Sham mice did not significantly differ in total amount of activity or in average active/inactive bout lengths during the light phase (7:00 am to 7:00 pm), when mice are typically less active.

In order to further dissect the nature of the shortened activity bouts after TBI, the frequency of bouts of varying duration, ranging from 10-20 minutes, 20-30 minutes, and greater than 30 minutes in length were examined during the dark phase. While the vast majority of bout durations are less than 10 minutes in length for both groups of mice, TBI mice have significantly more bouts in the 10-20 minute range and significantly fewer bouts greater than 30 minutes in length compared to Sham controls, throughout the acute, subacute and chronic time blocks (FIG. 6E).

TBI and Sham mice did not show the same magnitude of activity differences during the light phase, compared to the dark phase, but the pattern of decreased and shortened activity bouts was still evident in brain injured mice.

The total number of transitions between continuous Active and Inactive Bouts was significantly increased after TBI across the three time blocks (FIG. 6F). This indicates that there is significant fragmentation of activity bouts in injured mice.

To investigate whether diurnal rhythms were affected in TBI mice, actograms were plotted over the entirety of the 30 day activity monitoring period. Gross diurnal activity rhythms were intact in both Sham and TBI mice, consistent with the phenotype of an intact circadian clock. This indicates that TBI affects activity mechanisms downstream of the clock.

Taken together, the locomotor activity monitoring data demonstrate that a single episode of mild injury causes persistent alterations in activity lasting at least 30 days. Given that locomotor activity is highly predictive of behavioral state, this data indicates there are injury-induced alterations in sleep and wakefulness. In particular, brain injured mice show greater differences during the dark phase, when mice are typically more awake. Therefore, it was hypothesized that there would be specific deficits in the ability to sustain wakefulness.

Baseline EEG/EMG Recording: Inability to Sustain Wakefulness, Improved by BCAA Intervention To investigate the behavioral mechanisms underlying injury-induced decreases in activity, mice were implanted with chronic indwelling EEG/EMG electrodes. Behavioral states were analyzed over a five day period following an initial 7 day recovery period from surgery (FIG. 7). Because FPI causes changes in brain network excitability which are normalized by administration of dietary branched chain amino acids (BCAA), EEG/EMG recordings were performed on a separate cohort of injured mice on BCAA therapy. It was hypothesized that deficits in sleep-wake network excitability would be ameliorated by this dietary supplement in the drinking water.

Baseline recordings consisted of 24 hour periods from 7:00 am to 7:00 am. During baseline conditions, TBI mice spend significantly less time awake over both the light and dark phases, and more time in NREM sleep during the dark phase compared to Sham controls (FIG. 8A). TBI+BCAA mice show a partial reversal of changes in wake and NREM states. These results indicate that the decrease in activity measured using locomotor monitoring is explained by reduced wakefulness and increased NREM sleep.

Hypnograms were calculated for each animal by plotting wake, NREM and REM stages consecutively epoch-by-epoch over a 24 hour period, beginning with Lights On at 7:00 am. Naïve adult C57Bl6 wildtype mice typically show long bouts of wakefulness during the dark phase, particularly at the start of lights off, whereas orexin-deficient mice lack long wake bouts (Sakurai, T. (2007) Nat. Rev. Neurosci., 8:171-181). Sample hypnograms from Sham, TBI and TBI+BCAA mice are shown in FIG. 8B. Sham mice maintain long wake bouts at 7:00 pm Lights Off, while TBI mice continue to have fragmented wake bouts. BCAA intervention reinstates prolonged wake episodes.

Average continuous wake bout lengths were quantified over the 24 hour circadian cycle, subdivided into 3 hour bins beginning with Lights On at 7:00 am (or Zeitgeber Time (ZT) 0). TBI mice showed significantly shorter wake bouts in both the light and dark phases compared to Sham mice (FIG. 8C). This is particularly marked in the early part of the lights off period. Injured mice are unable to achieve long bouts of wakefulness compared to Sham control mice. BCAA therapy significantly lengthens wake bouts throughout the 24 hour cycle, thereby improving normal maintenance of wakefulness, but does not completely restore the ability to sustain wakefulness to control levels (FIG. 8C).

Average continuous sleep bout lengths were also quantified over the 24 hour circadian cycle, subdivided into 3 hour bins beginning as above. TBI mice have significantly shorter continuous sleep bouts during the dark phase compared to Sham mice, and this is partially restored with BCAA intervention, particularly during ZT 16-18, or 10:00 pm to 1:00 am (FIG. 8D).

Overall, these data indicate that TBI impairs the ability to sustain wakefulness and disrupts the normal diurnal fluctuation seen in wakefulness. The effect is most marked in the early part of the lights off period. BCAA therapy improves the ability to stay awake.

Baseline EEG/EMG Recording: Behavioral State Fragmentation, Rescued by BCAA Therapy To investigate the transitions between behavioral states in brain injury, the number of sleep and wake bout switches over the light and dark phases were quantified. During the dark phase, the total number of sleep-to-wake transitions (sleep=NREM and REM) was significantly increased in TBI mice compared to Sham mice, and BCAA intervention after TBI decreased the number of transitions back to Sham control levels (FIG. 9A).

Transition types were categorized into possible combinations between Wake, NREM and REM stages and subdivided by light and dark phases. TBI mice have more Wake to NREM (WN), NREM to Wake (NW), and REM to Wake (RW) transitions in comparison to Sham controls as well as in comparison to TBI with BCAA intervention during the dark phase (FIG. 9C). There were no significant differences between groups for transition subcategories during the light phase, when mice typically spend more time sleeping (FIG. 9B). This indicates that the transitions that specifically involve the wake state (i.e., WN, NW and RW) are most susceptible to injury.

In order to further characterize the nature of wake transitions, a histogram of varying wake bout durations was plotted (FIGS. 9D and 9E). During both the light and dark phases, TBI mice had significantly more bouts of shorter duration (in particular, less than 128 seconds in length) compared to Sham mice. BCAA therapy completely rescued this left shift towards shorter bout durations in the histogram. Bouts were also analyzed in NREM and REM sleep during the light and dark phases. While the most pronounced group differences are during the wake state, there is a similar, consistent pattern of shorter bouts after injury during NREM and REM states, indicating some degree of sleep fragmentation.

Taken together, these data highlight the severity of fragmentation during wakefulness, and also to a lesser degree also during sleep, induced by mild TBI. Behavioral state fragmentation and excessive daytime sleepiness are phenomena frequently cited in sleep disorders such as narcolepsy and post-traumatic hypersomnia (Guilleminault et al. (2000) Neurology 54:653-659; Rao et al. (2008) Brain Inj., 22:381-386; Verma et al. (2007) J. Clin. Sleep Med., 3:357-362; Baumann et al. (2007) Brain 130:1873-1883).

Baseline EEG/EMG Sleep-Wake Recording: Power Spectral Analysis

Power spectral analysis is a widely accepted method used for quantification of EEG signals. The power spectral density reflects the distribution of signal power (calculated by fast Fourier Transform of the polygraphic signal) plotted over specific frequency bins.

Baseline polygraphic signals were analyzed for power spectra in various frequency bands for the different conditions (FIG. 10). Wake spectra for TBI mice were significantly lower at the theta frequency range compared to Sham control mice (FIG. 10A). This was also found in NREM and REM spectra for TBI mice (FIGS. 10B and 10C). Theta power was restored by BCAA for spectra in the NREM state. Power spectra were further categorized by sleep stage and light/dark phases, which highlight group differences in particular for wake spectra during the dark and NREM/REM spectra during the light.

Because robust group differences in theta power were found, this effect was further evaluated by calculating the theta peak frequency for each behavioral state. Theta peak frequency was derived as the frequency value between 5 and 8 Hz with the maximum power density. In both wake and REM states, theta peak frequency for TBI mice was significantly slower compared to Sham control mice. BCAA therapy increased theta peak frequency, albeit not to control levels (FIGS. 10A and 10C).

Power density for specific frequency bands was calculated during each behavioral state. Group differences were noted in alpha, beta and gamma power densities, with injured mice showing a decrease in all three compared to Sham mice, with partial improvement in some bands with BCAA therapy.

Taken together, the power spectral analyses demonstrate that mild TBI produces persistent alterations in EEG rhythms. In particular, injury reduces theta power and shifts the theta peak to slower frequencies. This phenotype is ameliorated with BCAA intervention.

EEG/EMG Recording during a Novel Environment Challenge

Next, it was determined whether injury affects behavioral state in situations that challenged the arousal system. Mice were exposed to a novel environment at the start of the dark phase. The latency to first sleep episode was calculated for the two hour behavioral test (FIG. 11A). TBI mice had a shorter latency to sleep compared to Sham mice, and this shorter latency was partially restored by BCAA intervention (F=2.805, p=0.0923, Sham v. TBI p=0.05; one-way ANOVA with Dunnett's post-hoc test). Next, a chronological plot of wakefulness was calculated by tallying the total number of wake epochs per 5 minute bins. This plot showed that TBI mice had consistently lower percentage of wake epochs throughout the two hour test, with increasing propensity to sleep as the test went on (FIG. 11B). Sham control and BCAA therapy mice were indistinguishable, indicating that BCAA restore normal arousal and wakefulness during exposure to novelty.

EEG/EMG Recording After Mild Sleep Deprivation

The second wake challenge consisted of examining EEG response to a 3 hour period of enforced wakefulness using sleep deprivation by gentle handling. The wake challenge was performed from 10:00 am to 1:00 pm, which is a period of high sleep pressure in mice. The 3 hour period was chosen as an abbreviated length of time during which naïve mice typically do not show much sleep rebound, so as to maximize effect size (Franken et al. (1991) Neurosci. Lett., 130:141-144). Data from the following six hours from 1:00 to 7:00 pm, or "Recovery Sleep," were analyzed for NREM time, NREM bout length, NREM delta power and chronological percentage of wakefulness (FIG. 12).

TBI mice spent significantly more time in NREM sleep in the first hour immediately after sleep deprivation compared to Sham controls and mice receiving BCAA therapy (FIG. 12A). Interestingly, despite having more NREM sleep, TBI mice had shorter NREM bout lengths (FIG. 12B). Delta power during NREM sleep is widely accepted to be an accurate proxy for sleep pressure after a period of sleep deprivation (Franken et al. (1991) Neurosci. Lett., 130:141-144; Franken et al. (1991) Am. J. Physiol., 261:R198-208). TBI mice showed more delta power in the second hour during Recovery Sleep compared to Sham and TBI+BCAA mice (FIG. 12C). The chronological plot of wakefulness was low in all three groups, but appeared lowest in the TBI group compared to Sham and TBI+BCAA mice, particularly within the first two hours (FIG. 12D).

Taken together, these data indicate that mild brain injury imparts an increased pressure to sleep after situations of enforced arousal. However, despite increased sleep pressure, TBI mice are still unable to sustain long NREM sleep bouts. BCAA intervention improves and prolongs wakefulness after mild sleep deprivation.

Orexin Neuron Activation is Decreased After TBI and Restored by BCAA Intervention The phenotype of daytime sleepiness and state instability resembles the phenotype caused by orexin dysfunction (Sakurai, T. (2007) Nat. Rev. Neurosci., 8:171-181). Accordingly, orexin dysfunction was potentially contributing to the phenotype of injury-induced sleep disturbances. To test this hypothesis, orexin neuron activation was examined in response to a 3 hours period of enforced wakefulness from 10:00 am to 1:00 pm—the same paradigm used in the wake challenge test described above. Mice were 4 weeks post-TBI or Sham surgery, and a third group of mice received BCAA dietary supplementation for 4 weeks prior to sacrifice. Neural activation was measured by the presence of the immediate early marker c-Fos protein (Morgan et al. (1991) Annu. Rev. Neurosci., 14:421-451). Compared to Sham and TBI+BCAA groups, TBI mice had significantly fewer activated orexin neurons (FIG. 13C; F=22.47, p=0.0001; Sham v. TBI p=0.001, TBI v. TBI+BCAA p=0.01; one-way ANOVA with Dunnett's post-hoc test). Total orexin neuron numbers were not significantly different between groups, indicating that injury affects the physiological balance, and not gross cell loss per se, of this sleep-wake circuit.

Sleep disturbances, including excessive daytime sleepiness and sleep maintenance insomnia, have been reported as one prominent and chronic disabling consequence of mild traumatic brain injury (TBI). Early intervention of sleep problems would not only improve quality of life, but would also facilitate cognitive and neurobehavioral recovery after brain injury. The data presented herein are the first to establish a mouse model of chronic sleep/wake disturbances after mild TBI, namely, a persistent inability to maintain wakefulness. Herein, the locomotor activity and EEG-based behavioral states after a single mild non-penetrating head injury in mice are extensively characterized. It is then shown that orexin neuron activation is decreased in response to a wake stimulus, indicating alterations in orexin network excitability, similar to what has been described for hippocampal networks after injury (Cole et al. (2010) Proc. Natl. Acad. Sci., 107:366-371).

Given that the data show injury-induced deficits in orexin neuron activation, an intervention which restores orexin network excitability, thereby restoring wakefulness, would be effective. Indeed, dietary branched chain amino acids (BCAA) intervention rescued most sleep/wake disturbances, including increasing wake time, consolidating sleep and wake bouts, and raising arousal level to that seen in control mice during situations of heightened wakefulness. BCAA therapy achieves this effect by restoring EEG power spectral peaks, in particular theta power, and reinstating activation of orexin neurons during wakefulness.

It was found that a single mild brain injury causes persistent alterations in activity patterns, notably for over 4 weeks post-injury. This prolonged time course of disease is consistent with sleep and fatigue symptoms reported in the human condition (Verma et al. (2007) J. Clin. Sleep Med., 3:357-362; Kempf et al. (2010) J. Neurol. Neurosurg. Psychiatry 81:1402-1405). The persistence of symptoms indicates a secondary cascade of effects post-injury that chronically alters brain physiology.

A single mild brain injury also causes profound deficits in brain EEG at a snapshot in time at 2 weeks post-injury. Injured mice show deficits primarily in the dark phase, when mice are typically most active. During the dark phase, injured mice sleep more and are unable to sustain long bouts of wakefulness. They have more fragmented behavioral states and lose the normal diurnal fluctuation in wake bout length. This is consistent with seemingly paradoxical complaints of daytime sleepiness and nighttime insomnia frequently reported in both TBI and narcolepsy patients alike (Verma et al. (2007) J. Clin. Sleep Med., 3:357-362; Castriotta et al. (2010) CNS Drugs 25:175-185; Baumann et al. (2007) Brain 130:1873-1883). In addition, injured mice were unable to sustain wakefulness in situations requiring increased arousal, such as exposure to a novel environment, and showed increased sleep pressure after these short periods of enforced wakefulness. This data indicates that injured mice have less so-called wake reserve, a concept perhaps similar to "cognitive reserve" in aging and neurodegenerative disease (Alexander et al. (1997) Am. J. Psychiatry 154:165-172). It is possible that the widely reported symptoms of fatigue and inattention described after concussion could, in fact, reflect the same mechanisms underlying decreased wake reserve (Dockree et al. (2004) Brain Res. Cogn. Brain Res., 20:403-414).

After injury, there is an overall shift in EEG power density to slower frequencies during the wake state, in particular for theta power. Slowing of theta peak frequency has been implicated in aging and hippocampal-dependent cognitive deficits (Colas et al. (2005) Neurobiol. Aging 26:265-273; Perouansky et al. (2010) Anesthesiology 113:1299-1309). Interestingly, the same left shift in power spectrum is seen in patients with Alzheimer's disease, thought to reflect functional disconnections among cortical areas (Moretti et al. (2011) Front Psychiatry 1:152; Jeong, J. (2004) Clin. Neurophysiol., 115:1490-1505). Similarities in EEG pathology may reflect shared neuropathological mechanisms between TBI and Alzheimer's disease.

Because of similarities in phenotype to human narcolepsy, and human TBI studies implicating dysfunction of the orexin system, alterations in the expression of the neuropeptide orexin was investigated. The involvement of other candidate wake-promoting regions of the brain is less likely given that lesions of such regions (i.e., ventral periaqueductal gray, locus coeruleus, basal forebrain) do not precisely fit the TBI phenotype of sleep fragmentation superimposed on the inability to sustain wakefulness (Lu et al. (2006) J. Neurosci., 26:193-202; Gompf et al. (2010) J. Neurosci., 30:14543-14551; Blanco-Centurion et al. (2007) J. Neurosci., 27:14041-14048). In support of orexin's involvement, several human studies have reported deficits in orexin after TBI. One small study of 4 patients who died 7 to 42 days after severe TBI showed a 27% reduction in the number of orexin neurons compared to non TBI controls (Baumann et al. (2009) Ann. Neurol., 66:555-559). Measured levels of CSF orexin were low in 95% of 44 patients within the first four days of moderate to severe TBI, with the lowest levels of CSF orexin observed in patients who were comatose (Baumann et al. (2005) Neurology 65:147-149). When CSF orexin was measured in these same patients 6 months post-injury, 4 of the 14 patients with excessive daytime sleepiness continued to have low orexin levels, while those without daytime sleepiness showed normalization of CSF orexin levels (Baumann et al. (2007) Brain 130:1873-1883). Controlled-cortical impact (moderate, penetrating brain injury) acutely decreased brain orexin levels in mice, as measured by intracerebral microdialysis within the first three days of injury (Lim et al. (2012) J. Neurotrauma 29:1908-1921). The total number of orexin neurons was unchanged after injury, in contrast to the findings in the small human study, though this likely is explained by differences between mild/moderate versus severe TBI (Lim et al. (2012) J. Neurotrauma 29:1908-1921; Baumann et al. (2009) Ann. Neurol., 66:555-559). The data provided herein indicates that mild/moderate brain injury primarily affects orexin physiology rather than gross cell loss, at least in the immediate weeks following injury.

While the exact mechanisms of injury-induced wake dysfunction are unknown, it is clear that BCAA intervention restores many aspects of wakefulness, including underlying deficits in EEG oscillations and orexin neuron activation. BCAA therapy restores network excitability and hippocampal-dependent cognitive deficits, possibly by restoring pools of releasable vesicular glutamate and GABA (Cole et al. (2010) Proc. Natl. Acad. Sci., 107:366-371). Indeed, glutamate inputs to orexin neurons are well documented to regulate wakefulness, and glutamatergic interneurons have been suggested to play a role in a positive feedback recruitment of orexin on orexin neurons (Acuna-Goycolea et al. (2004) J. Neurosci., 24:3013-3022). In addition, dietary amino acids have been shown to directly affect orexin neuron membrane excitability; this macronutrient sensing mechanism is thought to explain the role of orexin in appetite (Karnani et al. (2012) Neuron 72:616-629).

Branched chain amino acids are essential amino acids and cannot be synthesized de novo, and therefore must be acquired through the diet. Once in the brain, the three BCAA (L-Leucine, L-Valine, and L-isoleucine) are key amino acids involved in de novo glutamate synthesis, as approximately 50% of brain glutamate and 40% of the releasable synaptic glutamate contains BCAA-derived nitrogen (Yudkoff, M. (1997) Glia 21:92-98; Sakai et al. (2004) J. Neurochem., 88:612-622). In a small number of human studies, plasma BCAA levels were decreased with mild and severe TBI, and one follow-up study found that IV BCAA therapy in severe TBI yielded improvement in disability outcomes (Jeter et al. (2013) J. Neurotrauma 30:671-679; Vuille-Dit-Bille et al. (2012) Amino Acids 43:1287-1296; Aquilani et al. (2005) Arch. Phys. Med. Rehabil., 86:1729-1735). Dietary BCAA administration has been studied extensively in healthy people and in disease states over many decades (Fernstrom, J.D. (2005) J. Nutr., 135:1539S-1546S). Patients with a variety of disorders (including liver cirrhosis, bipolar disorder, spinocerebellar degeneration, to name a few), have been treated with BCAA's for variable lengths of time longer than 2 years without adverse effects (Muto et al. (2005) Clin. Gastroenterol. Hepatol., 3:705-713). Overall, BCAA therapy is well tolerated and associated with minimal to no side effects, and therefore is a viable therapy for mild TBI.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating a sleep disorder associated with traumatic brain injury in a subject, said method comprising administering to said subject a composition comprising valine, leucine and isoleucine in an amount sufficient to restore wakefulness in the subject.

2. The method of claim 1, wherein said sleep disorder is selected from the group consisting of sleep-wake fragmentation, insomnia, fatigue, drowsiness, sleep apnea, narcolepsy, excessive daytime sleepiness, decreased wakefulness, and increased non-rapid-eye-movement (NREM) sleep.

3. The method of claim 1, wherein orexin neuron activation is restored after administration of the composition.

4. The method of claim 1, wherein said composition is administered to the subject prior to sleep.

5. The method of claim 1, wherein said composition is administered to the subject within 4 days of said traumatic brain injury.

6. The method of claim 1, wherein said composition is administered to the subject for at least 10 consecutive days.

7. A method of treating an injury-induced sleep disturbance in a subject, said method comprising administering to said subject a composition comprising valine, leucine and isoleucine in an amount sufficient to restore wakefulness in the subject.

8. The method of claim 7, wherein said sleep disturbance is selected from the group consisting of sleep-wake fragmentation, insomnia, fatigue, drowsiness, sleep apnea, narcolepsy, excessive daytime sleepiness, decreased wakefulness, and increased non-rapid-eye-movement (NREM) sleep.

9. The method of claim 7, wherein orexin neuron activation is restored after administration of the composition.

10. The method of claim 7, wherein said composition is administered to the subject prior to sleep.

11. The method of claim 7, wherein said composition is administered to the subject within 4 days of said injury.

12. The method of claim 7, wherein said composition is administered to the subject for at least 10 consecutive days.

13. A method of restoring or increasing wakefulness in a subject having a traumatic brain injury, said method comprising administering to said subject a composition comprising valine, leucine and isoleucine in an amount sufficient to restore or increase wakefulness in the subject.

14. The method of claim 13, wherein orexin neuron activation is restored after administration of the composition.

15. The method of claim 13, wherein said composition is administered to the subject prior to sleep.

16. The method of claim 13, wherein said composition is administered to the subject within 4 days of said traumatic brain injury.

17. The method of claim 13, wherein said composition is administered to the subject for at least 10 consecutive days.

* * * * *